United States Patent
Pang et al.

(10) Patent No.: US 9,499,528 B2
(45) Date of Patent: Nov. 22, 2016

(54) CLASS OF NEAR INFRARED MOLECULAR PROBES FOR BIOLOGICAL APPLICATIONS

(71) Applicants: Yi Pang, Copley, OH (US); Junfeng Wang, Akron, OH (US)

(72) Inventors: Yi Pang, Copley, OH (US); Junfeng Wang, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 14/247,812

(22) Filed: Apr. 8, 2014

(65) Prior Publication Data

US 2014/0303376 A1    Oct. 9, 2014

Related U.S. Application Data

(60) Provisional application No. 61/809,492, filed on Apr. 8, 2013.

(51) Int. Cl.
*C07D 401/00* (2006.01)
*C07D 413/14* (2006.01)

(52) U.S. Cl.
CPC .................................. *C07D 413/14* (2013.01)

(58) Field of Classification Search
CPC ..................................................... C07D 413/14
USPC ......................................................... 546/256
See application file for complete search history.

(56) References Cited

U.S. PATENT DOCUMENTS 9,090,602 B2 * 7/2015 Pang ..................... G01N 33/52
2014/0080168 A1   3/2014 Pang

FOREIGN PATENT DOCUMENTS

WO    2010075003    7/2010

OTHER PUBLICATIONS

Mukhopadhyay, Tetrahedron Letters, 2008, 49, 6237-6240.*
Xu, et al.; Zn2-Triggered excited state intermolecular proton transfer: a sensitive probe with near-infrared emission from bis(benzoxazole) derivative, 2011, Dalton Trans, vol. 40 pp. 1503-1509 (2011).
Luzina, et al.; Effect of alkyl substituents on excited state intramolecular proton transfer dynamics of jet-cooled bis (benzoxazolyl)phenoles, The Journal of Chemical Physics: vol. 126, pp. 194308-1-1 (2007).
Xu, et al.; Binding-Enabled Excited State Intramolecular Proton Transfer: A Step toward New Near-Infrared Fluorescent Propes for Imaging Applications; Advanced Healthcare Materials; vol. 1, Issue 4, pp. 485-492 (2012).
Mukhopadhyay et al., Tetrahedron Letters, 2008, 49, 6237-6240.

* cited by examiner

*Primary Examiner* — Nizal Chandrakumar
(74) *Attorney, Agent, or Firm* — Renner Kenner Greive Bobak Taylor & Weber

(57) ABSTRACT

Methods for preparing 2,5-Bis(benzoxazol-2'-yl)benzene-1, 4-diol derivatives (Zinhbo derivatives) are provided. Zinhbo derivatives are used to detect zinc ions and have particular application in vivo and in vitro. Zinhbo derivatives upon excitation give a florescence response emission that can be used to determine the presence of zinc cation in solution. Zinhbo derivatives complexed with zinc cations upon excitation can produce a florescence response emission in the visible and near infrared range. Zinhbo derivatives complexed with zinc cations exhibit a large stoke shift between the excitation and emission wavelengths.

13 Claims, 9 Drawing Sheets

CLASS OF NEAR INFRARED MOLECULAR PROBES FOR BIOLOGICAL APPLICATIONS

This application claims priority from U.S. provisional patent application Ser. No. 61/809,492 filed on Apr. 8, 2013, which is incorporated herein by reference in its entirety.

FIELD OF THE INVENTION

The present invention generally relates to compounds for the detection of zinc ions, the synthesis of compounds for the detection of zinc ions, compositions for the detection zinc ions, and methods for detecting zinc ions.

BACKGROUND OF THE INVENTION

Organic fluorescent probes are useful labeling for biomolecules. For in vivo applications, molecular imaging reagent is required to be biocompatible and to emit optical signals in the near infrared (NIR) region (700-900 nm), as NIR light can penetrate more deeply into biological tissues. On the practical side, optical imaging is dependent on the availability of the luminescent NIR reagents that exhibit high quantum yield, chemical and optical stability, and suitable pharmacological properties including aqueous solubility, specific binding, and low toxicity. At present time, most of the NIR probes are based on cyanine dyes, whose emission maxima are in the region of 650-900 nm. A notable drawback for the parent cyanine dyes is their small Stokes shift (typically about 20-50 nm), which hampers their broad application.

Among the new emerging design principles applied in fluorescent sensing, excited-stated intramolecular proton transfer (ESIPT) has recently received considerable attention due to its unique photophysical properties. Different from other organic chromophores, ESIPT molecules exhibit dual emissions from both the excited enol and keto tautomers, which are well separated from each other. In addition, emission of ESIPT dyes generally have large Stokes shift (ca. 150-200 nm), making them the ideal candidates for fluorescent sensors. Some ESIPT-based molecules, including 2-(2'-hydroxyphenyl)benzoxazole (HBO) and 2-(2'-hydroxyphenyl)benzimidazole (HBI), have been reported for cations and anion sensing. Most studies utilize ESIPT turn-off mechanisms since the interaction with a cation (or anion) removes the phenolic proton, thereby inhibiting ESIPT and resulting in blue-shifted fluorescence. Removal of the phenolic proton during metal chelation, however, permanently turns-off ESIPT. Thus far, only a few examples are known to utilize ESIPT turn-on mechanism in the chemosensor design, which involves the deprotection of the protected hydroxyl group. Among the known examples, nearly all ESIPT-based probes give emission in the visible region (400-650 nm).

As the second most abundant transition-metal ion in the human body, the $Zn^{2+}$ ion is a component of enzymes and proteins, and plays an important role in various biological processes. In order to discover the vital roles of $Zn^{2+}$ in biological processes, there is growing demand for sensing $Zn^{2+}$ in living systems. Although many fluorescent chemosensors for $Zn^{2+}$ cation have been studied, few near-infrared (NIR) fluorescent zinc probes are available to give emission in the desired 700-900 nm range. An ideal $Zn^{2+}$ probe requires not only NIR emission (to minimize autofluorescence) but also large Stokes shift (for improved signal detection). It is thus desirable to incorporate the ESIPT process into the sensing scheme. Achieving the ESIPT emission signals in the NIR region, however, remains an attractive and challenging task.

SUMMARY OF THE INVENTION

One or more embodiments of this invention provides a process of preparing a Zinhbo derivative comprising:
(i) reacting a protected compound by the formula:

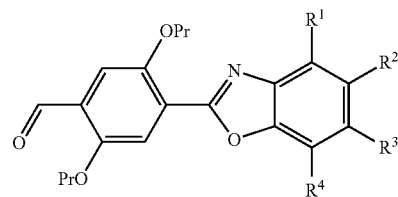

where Y is an oxygen atom, a sulfur atom, a nitrogen atom with a pendant hydrogen atom, or a nitrogen atom with a pendant alkyl group; each Pr is individually a protecting group and $R^1, R^2, R^3$, and $R^4$ are each individually selected from the group consisting of a hydrogen atom, an electron withdrawing group, and an electron donating group, with a the 2-aminophenol derivative containing a zinc-binding ligand is defined by the formula

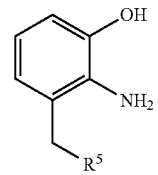

where $R^5$ is a chelating group attached through a nitrogen atom; and
(ii) deprotecting the protecting groups.

One or more embodiments of this invention also provides a process for preparing a Zinhbo derivative comprising:
(i) reacting a protected compound defined by the formula:

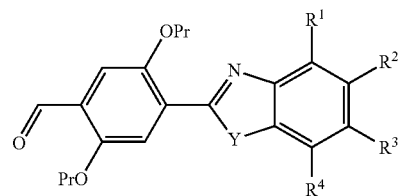

where Y is an oxygen atom, a sulfur atom, a nitrogen atom with a pendant hydrogen atom, or a nitrogen atom with a pendant alkyl group; each Pr is individually a protecting group and $R^1, R^2, R^3$, and $R^4$ are each individually selected from the group consisting of a hydrogen atom, an electron withdrawing group, and an electron donating group, with a 2-aminophenol derivative defined by the formula

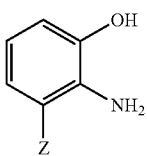

where Z is a carboxylic acid, a protected ester or a hydroxymethyl group, to prepare a molecule defined by the formula I:

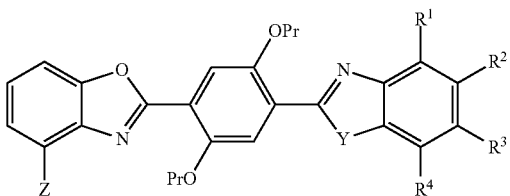

where Z is a carboxylic acid, a protected ester or a hydroxymethyl group: Y is an oxygen atom, a sulfur atom, a nitrogen atom with a pendant hydrogen atom, or a nitrogen atom with a pendant alkyl group; each Pr is individually a protecting group; and $R^1$, $R^2$, $R^3$, and $R^4$ are each individually selected from the group consisting of a hydrogen atom, an electron withdrawing group, and an electron donating group;
(ii) converting the Z group to a halogen atom or tosyl group;
(iii) reacting the halogen atom or tosyl group with a an amine compound that includes a chelating group; and
(iv) deprotecting the protecting groups.

One or more embodiments of this invention also provides a Zinhbo derivative defined by the formula:

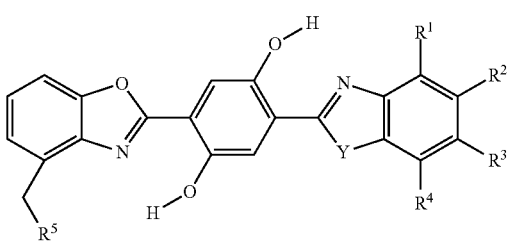

where $R^1$, $R^2$, $R^3$, and $R^4$ are each individually selected from the group consisting of a hydrogen atom, an electron withdrawing group, and an electron donating group; Y is a sulfur atom, a nitrogen atom with a pendant hydrogen atom, or a nitrogen atom with a pendant alkyl group; and $R^5$ is a chelating group attached through a nitrogen atom.

One or more embodiments of this invention also provides a Zinhbo derivative defined by the formula:

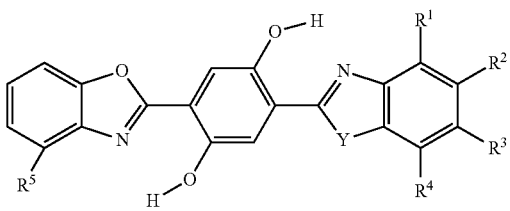

where $R^1$, $R^2$, $R^3$, and $R^4$ are each individually selected from the group consisting of a hydrogen atom, an electron withdrawing group, and an electron donating group; Y is a sulfur atom, a nitrogen atom with a pendant hydrogen atom, or a nitrogen atom with a pendant alkyl group; and $R^5$ is a chelator group capable of forming a complex with a zinc cation.

DETAILED DESCRIPTION OF ILLUSTRATIVE EMBODIMENTS

Figure 1:
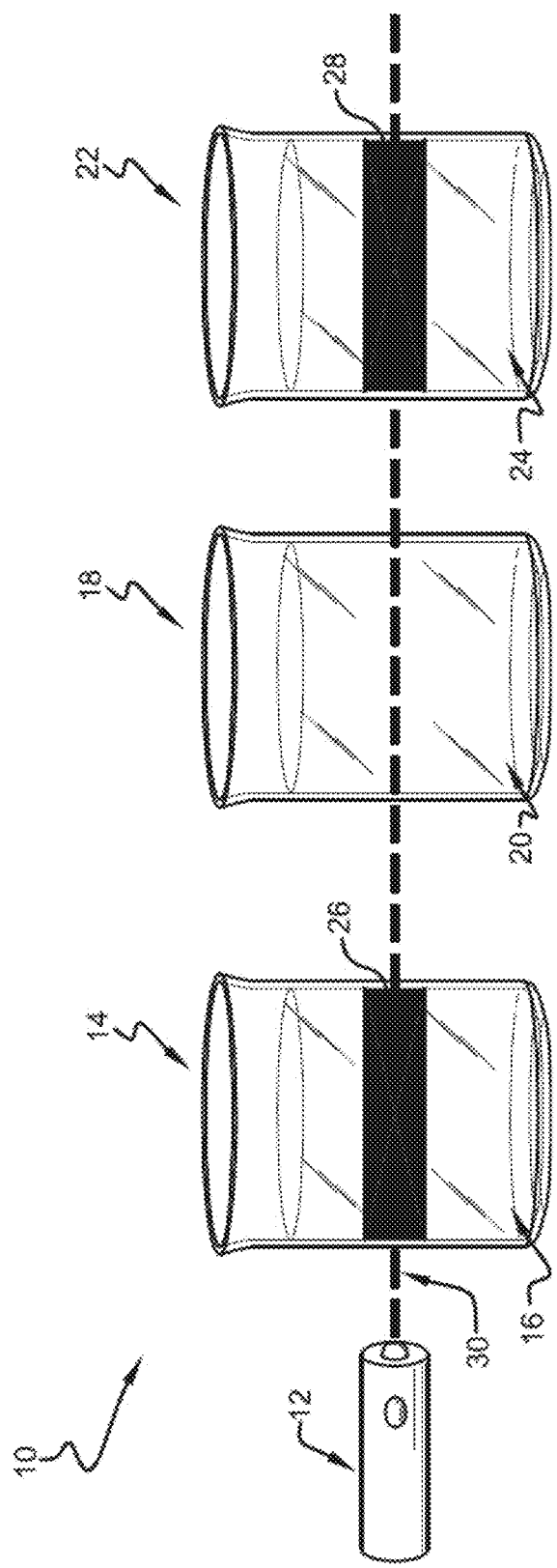
FIG. 1 provides a general schematic of a method for testing one or more test solutions for the presence of zinc cation in accordance with this invention.
Figure 2:
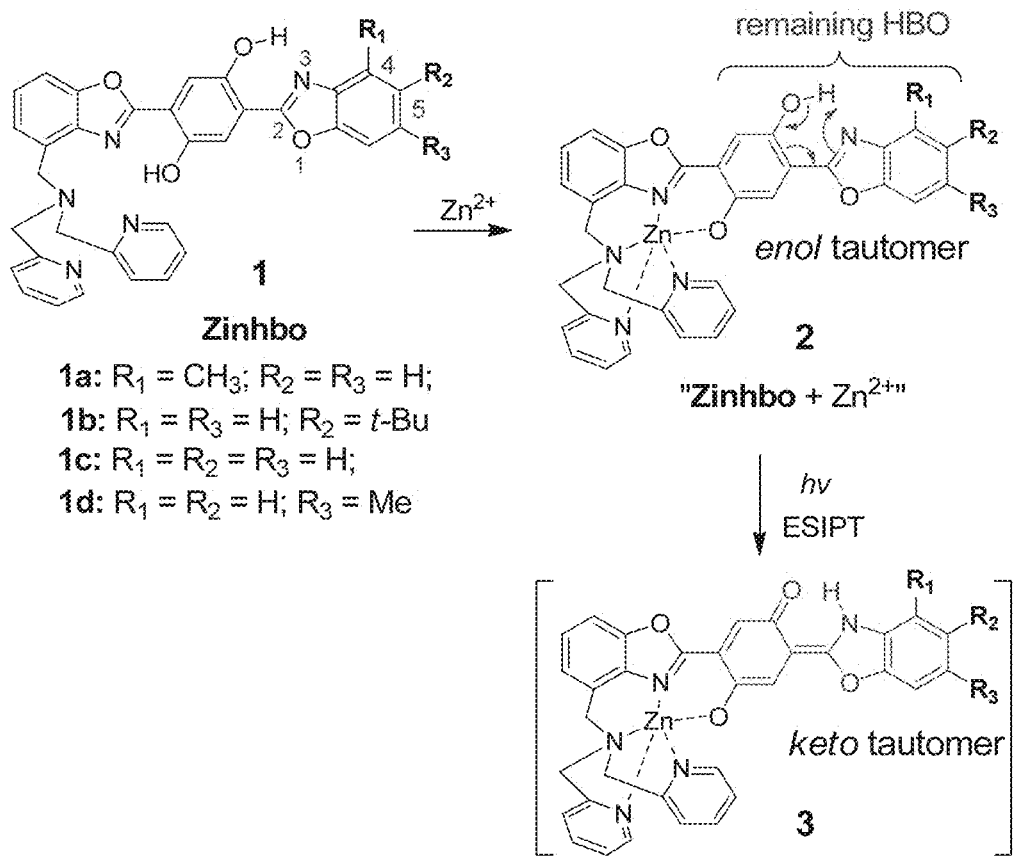
FIG. 2 provides Zinhbo compounds 1 and their corresponding zinc complexes, and the enol and keto tautomer structures.

One or more embodiments provides the synthesis of 2,5-bis(benzoxazol-2'-yl)benzene-1,4-diol derivatives for the detection of zinc ions. Also provided are compositions for the detections of zinc ions, and methods for the detection of zinc ions using 2,5-bis(benzoxazol-2'-yl)benzene-1,4-diol derivatives. These compositions and methods will have particular application in vivo and in vitro.

The applicants have found that 2,5-bis(benzoxazol-2'-yl)benzene-1,4-diol derivatives can give turn-on excited state intramolecular proton transfer (ESIPT) fluorescence upon addition of zinc cations. A unique feature of 2,5-bis(benzoxazol-2'-yl)benzene-1,4-diol derivatives is that the sensor molecule contains two 2-(2'-hydroxyphenyl)benzoxazole units. In its zinc complex only one 2-(2'-hydroxyphenyl)benzoxazole unit binds to a zinc cation, while the other 2-(2'-hydroxyphenyl)benzoxazole unit is retained for ESIPT. Zinc binding not only turns on the fluorescence but also enables the ESIPT emission with a large Stokes shift. In one or more embodiments, the 2,5-bis(benzoxazol-2'-yl) benzene-1,4-diol derivative binds a zinc cation that is a $Zn^{2+}$ cation. For further discussion on florescence of 2,5-bis (benzoxazol-2'-yl)benzene-1,4-diol derivatives see Y. Xu, Y. Pang, Chem. Commun., 46 4070-4072 (Apr. 15, 2010), Y. Xu, Y. Pang, Dalton Transactions, 40 1503-1509 (Feb. 1, 2011), and U.S. Pat. Pub. 2014/0080168 which are incorporated in their entirety by reference.

In one or more embodiments, 2,5-bis(benzoxazol-2'-yl) benzene-1,4-diol derivatives are compounds which include a dihydroxyphenyl group bound to two benzoxazole groups. In one or more embodiments, a benzoxazole group of the 2,5-bis(benzoxazol-2'-yl)benzene-1,4-diol derivative may include one or more groups that form a complex with a zinc ion. In one or more embodiments, a benzoxazole group of the 2,5-bis(benzoxazol-2'-yl)benzene-1,4-diol derivative may include one or more substituents that are electron donating groups and/or one or more substituents that are electron withdrawing groups. In these or other embodiments, the oxygen atom of the benzoxazole group of the 2,5-bis(benzoxazol-2'-yl)benzene-1,4-diol derivative may be substituted for a sulfur atom, a nitrogen atom with a pendant hydrogen atom, or a nitrogen atom with a pendant alkyl group. A 2,5-bis(benzoxazol-2'-yl)benzene-1,4-diol derivative may also be considered a compound which includes two 2-(2'-hydroxyphenyl)benzoxazole units that share a dihydroxyphenyl group. A 2-(2'-hydroxyphenyl) benzoxazole unit may also be referred to as a HBO unit. 2,5-Bis(benzoxazol-2'-yl)benzene-1,4-diol derivatives may be referred to as Zinhbo derivatives.

In one or more embodiments, the Zinhbo derivative may be defined by the following formula:

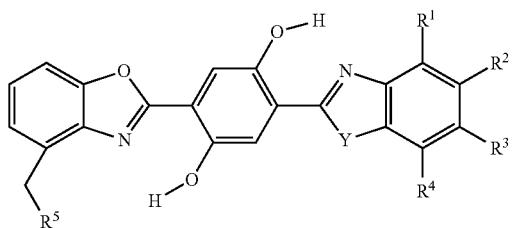

where $R^1$, $R^2$, $R^3$, and $R^4$ are each individually selected from the group consisting of a hydrogen atom, an electron withdrawing group, and an electron donating group; Y is an oxygen atom, a sulfur atom, a nitrogen atom with a pendant hydrogen atom, or a nitrogen atom with a pendant alkyl group; and $R^5$ is a chelating group attached through a nitrogen atom.

Suitable alkyl groups for use as a pendant alkyl group on a nitrogen atom include linear or branched hydrocarbons with a carbon chain length of 1 to 6 carbons. Specific examples of alkyl groups include, but are not limited to, methyl, ethyl, propyl, isopropyl, isobutyl, tert-butyl, n-butyl, sec-butyl, isopentyl, tertpentyl, n-pentyl, sec-pentyl, terthexyl, n-hexyl, isohexyl, and sec-hexyl.

Figure 3:
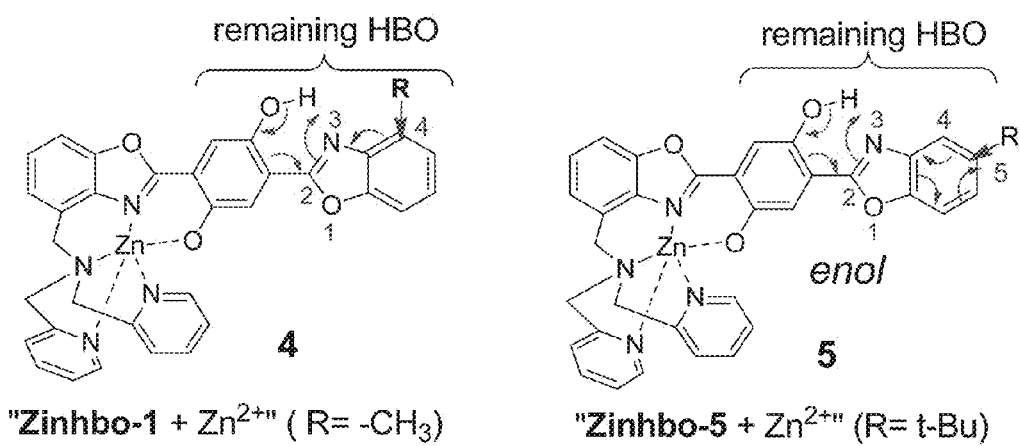
FIG. 3 provides the electron flow for the excited state intramolecular proton transfer (ESIPT) for two embodiments of Zinhbo molecules.
Figure 4:
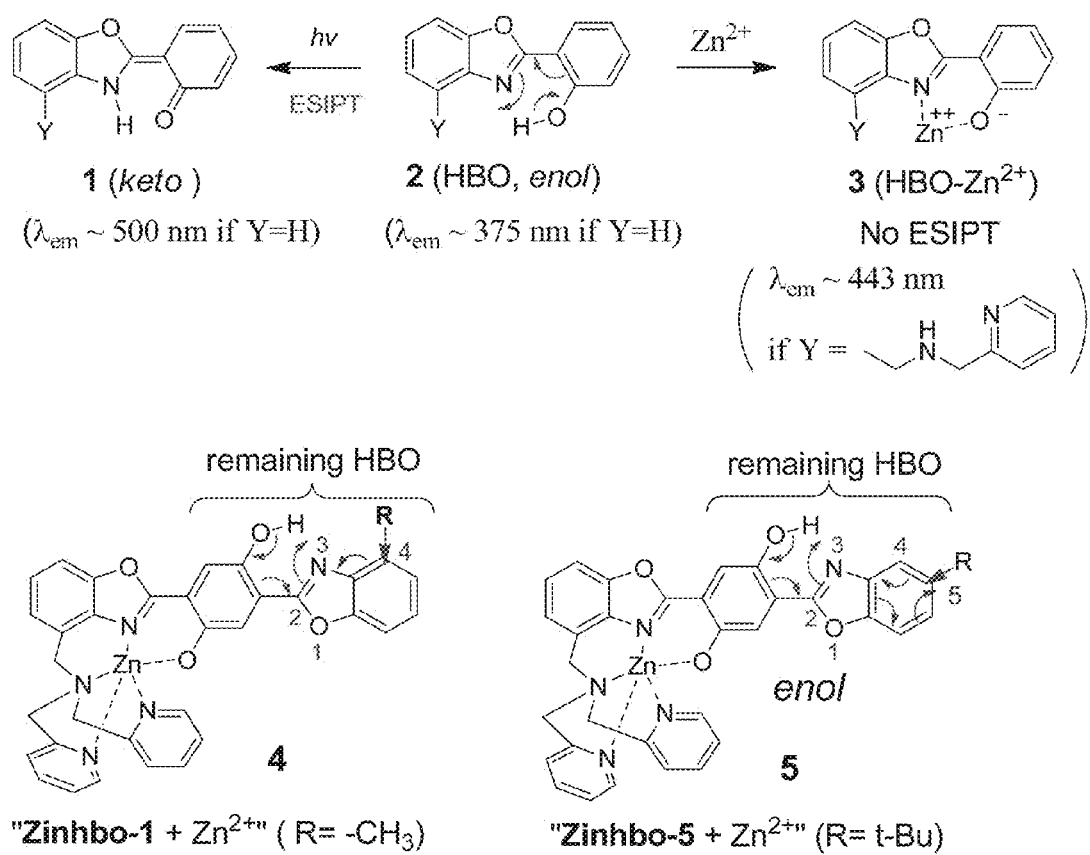
FIG. 4 provides the electron flow for the excited state intramolecular proton transfer (ESIPT) for various HBO and Zinhbo molecules.
Figure 5:
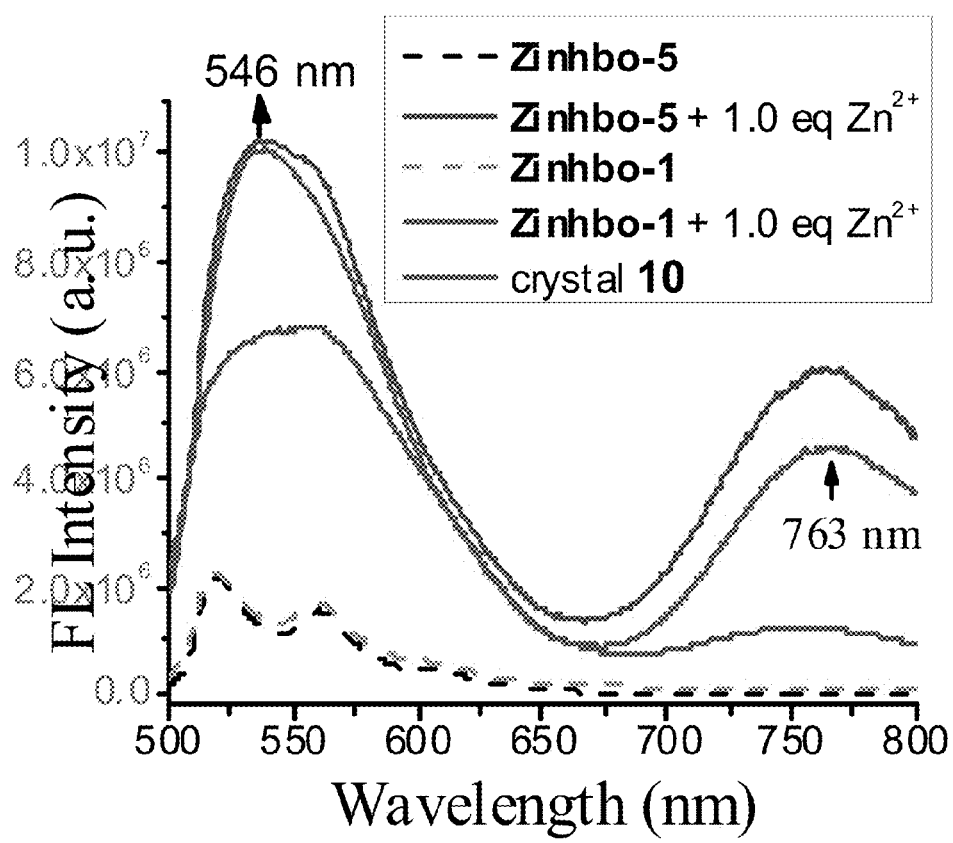
FIG. 5 provides the fluorescence spectra of Zinhbo-5 and Zinhbo-1 ($1.0 \times 10^{-5}$ M) upon addition of zinc cation in THF (excitation at 480 nm). $(Zinhbo-5)_2-Zn^{2+}$ (2:1 ligand-to-metal ratio) is the predominant form when $Zn^{2+}$ is added to Zinhbo-5 in solution.
Figure 6:
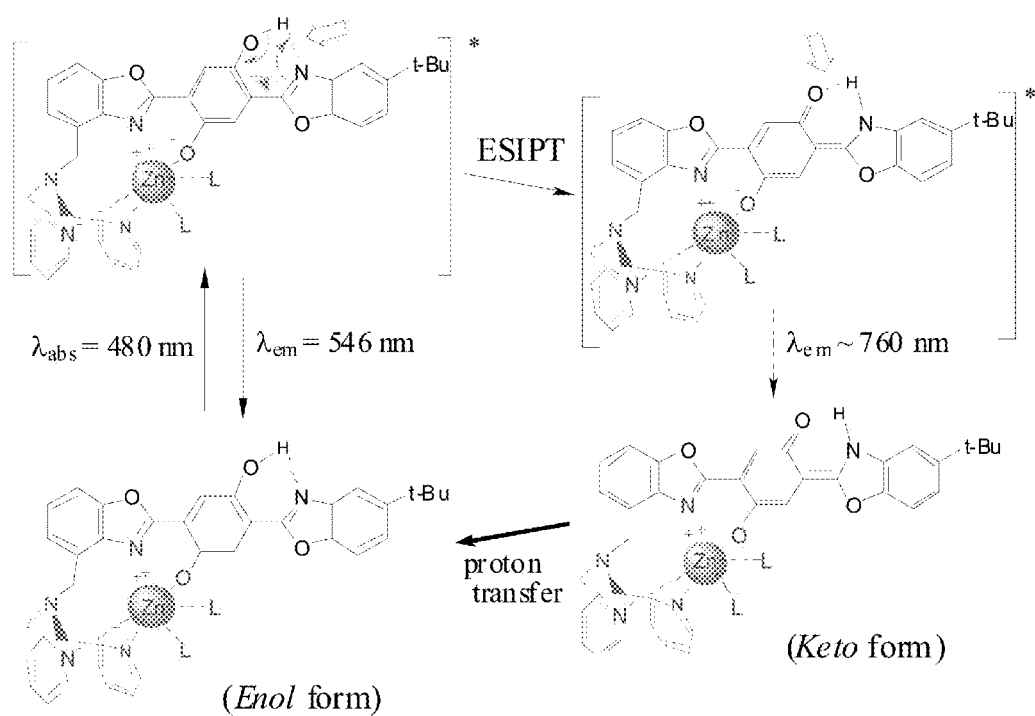
FIG. 6 provides a schematic representation of the ESIPT process of Zinhbo-5-Zn complex, involving the enol emission at 546 nm and keto emission at 763 nm. The thick arrows indicate the hydrogen bonds in the excited states.
Figure 7:
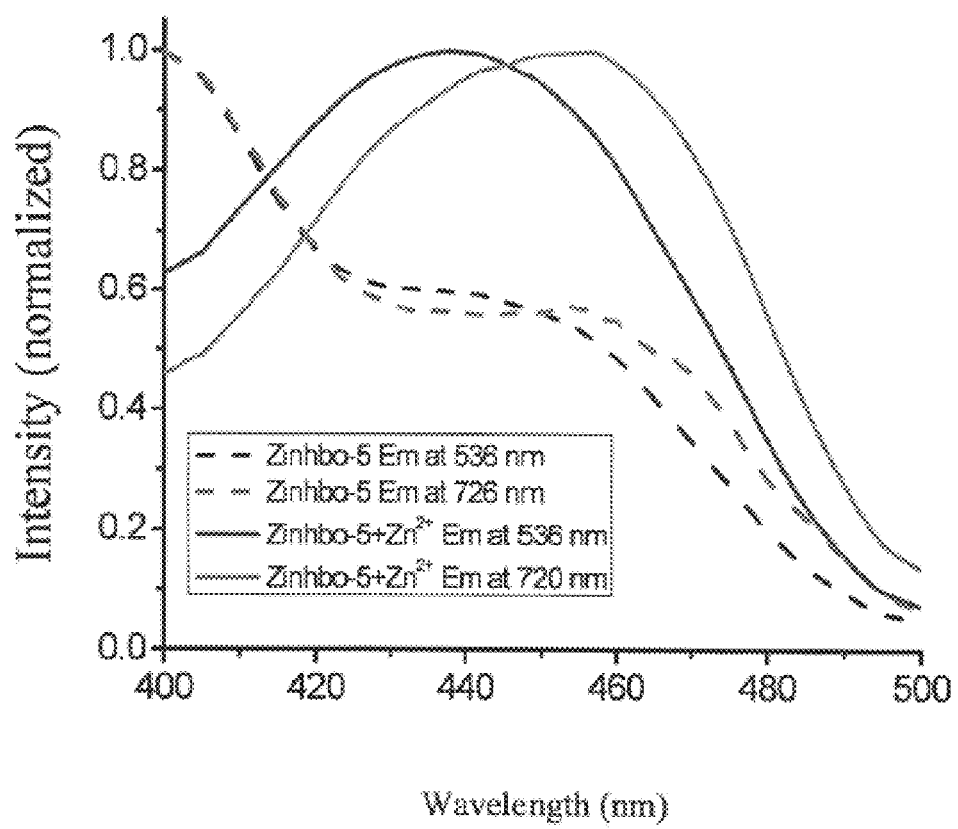
FIG. 7 provides a graph of the excitation spectra for Zinhbo-5 ($1.0 \times 10^{-5}$ M) in HEPES buffer solution containing 50% EtOH with and without 1 equivalent of zinc ions.
Figure 8:
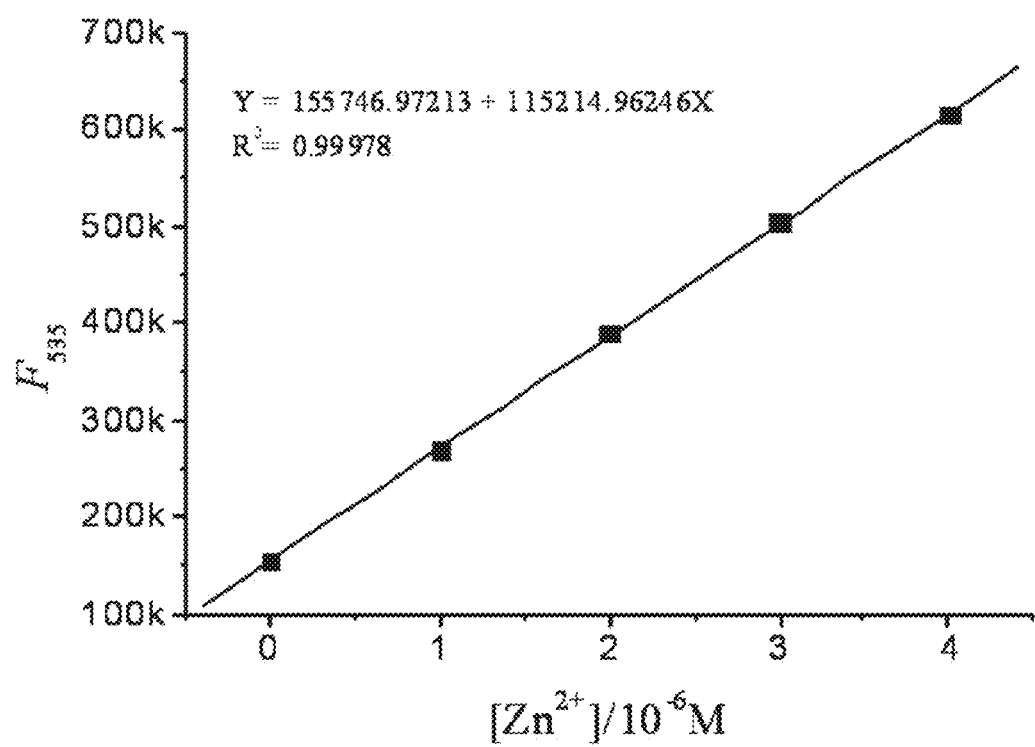
FIG. 8 provides a graph of the fluorescence intensity of Zinhbo-5 (10 μM) at 535 nm as a function of concentration of $Zn^{2+}$(0-4 μM) in $H_2O$/EtOH (5/5) solution (containing 50 M HEPES, 0.1M $KNO_3$, pH=7.2). The inset of FIG. 8 provides the emission spectra of Zinhbo-5 in the presence of different concentrations of $Zn^{2+}$ ion. The linearly dependent coefficient is: $R^2$=0.99978.
Figure 9:
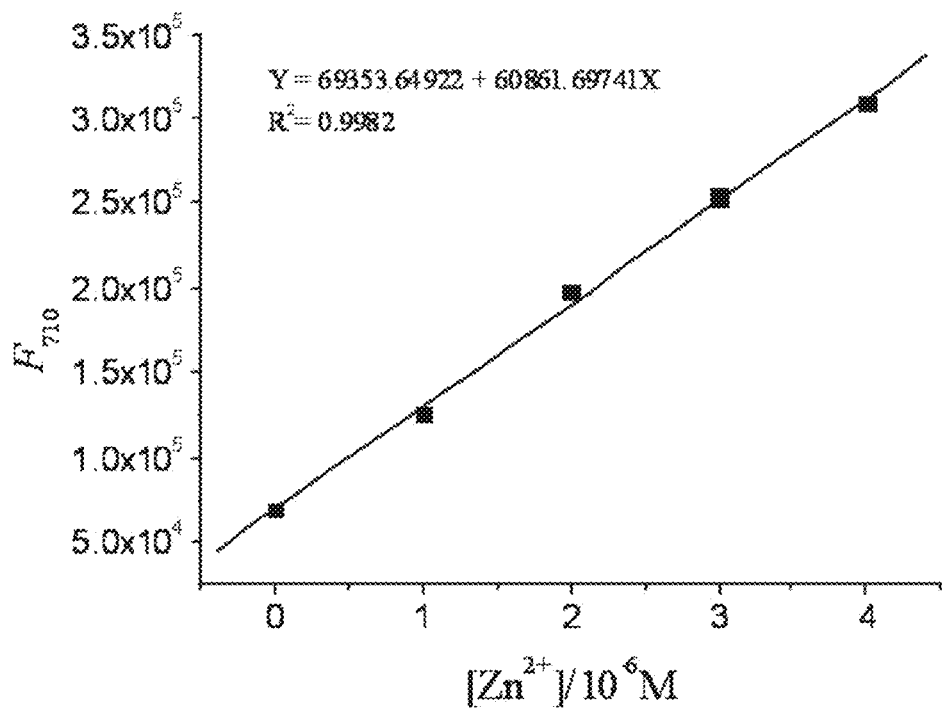
FIG. 9 provides a graph of the fluorescence intensity of Zinhbo-5 (10 μM) at 710 nm as a function of concentration of $Zn^{2+}$ (0-4 μM) in $H_2O$/EtOH (5/5) solution (containing 50 M HEPES, 0.1M $KNO_3$, pH=7.2). The inset of FIG. 9 provides the emission spectra of Zinhbo-5 in the presence of different concentrations of $Zn^{2+}$ ion. The linearly dependent coefficient is: $R^2$=0.9982.

In one or more embodiments, the $R^1$ of formula 1 is not an electron donating group. In these and other embodiments, $R^1$ of formula 1 is not an alkyl group. In these or other embodiments, $R^1$ of formula 1 is an electron withdrawing group or a hydrogen atom. Though not to be bound by any particular theory, it is believed that, when $R^1$ of formula 1 is an electron donating group the electron flow required for the excited-state intramolecular proton transfer is partially perturbed by the electron donating effect (FIG. 3).

Electron donating groups, also referred to as activating groups, are groups that add electron density to the benzene ring. Electron donating groups are typically classified by their strength into groups consisting of strong electron donating groups, moderate electron donating groups, and weak electron donating groups.

Examples of strong electron donating groups include, but are not limited to, an alcohol group (—OH), an oxyl group (—O⁻), an amino group (—$NH_2$), alkylamino groups (—NHR), and dialkylamino groups (—$NR_2$). Examples of moderate electron donating groups include, but are not limited to, alkoxy groups (—OR) and amide groups (—NH-COR). Examples of weak electron donating groups include, but are not limited to, alkyl groups (—R). For the purpose of defining donating groups R can be defined as an alkyl group. In one or more embodiments alkyl groups include linear or branched hydrocarbons with a carbon chain length of 1 to 6 carbons. Specific examples of alkyl groups include, but are not limited to, methyl, ethyl, propyl, isopropyl, isobutyl, tert-butyl, n-butyl, sec-butyl, isopentyl, tertpentyl, n-pentyl, sec-pentyl, terthexyl, n-hexyl, isohexyl, and sec-hexyl.

Specific examples of alkylamino groups suitable for use as an electron donating group include, but are not limited to, methylamino, ethylamino, propylamino, isopropylamino, isobutylamino, tert-butylamino, n-butylamino, sec-butylamino, isopentylamino, tertpentylamino, n-pentylamino, sec-pentylamino, terthexylamino, n-hexylamino, isohexylamino, and sec-hexylamino.

Specific examples of dialkylamino groups suitable for use as an electron donating group include, but are not limited to, dimethylamino, diethylamino, dipropylamino, diisopropylamino, diisobutylamino, di-tert-butylamino, di-n-butylamino, di-sec-butylamino, diisopentylamino, tertpentylamino, di-n-pentylamino, di-sec-pentylamino, di-tert-hexylamino, n-hexylamino, diisohexylamino, di-sec-hexylamino, methylethylamino, methylpropylamino, methylisopropylamino, methylisobutylamino, tert-butylmethylamino, n-butylmethylamino, ethylpropylamino, ethylisopropylamino, ethylisobutylamino, tert-butylethylamino, and n-butylethylamino.

In one or more embodiments, alkyl groups suitable for use as an electron donating group include linear or branched hydrocarbons with a carbon chain length of 1 to 6 carbons. Specific examples of alkyl groups suitable for use as an electron donating group include, but are not limited to, methyl, ethyl, propyl, isopropyl, isobutyl, tert-butyl, n-butyl, sec-butyl, isopentyl, tertpentyl, n-pentyl, sec-pentyl, terthexyl, n-hexyl, isohexyl, and sec-hexyl.

Specific examples of alkoxy groups suitable for use as an electron donating group include, but are not limited to, methoxy, ethoxy, propoxy, isopropoxy, isobutoxy, tert-butoxy, n-butoxy, sec-butoxy, isopentoxy, tertpentoxy, n-pentoxy, sec-pentoxy, terthexoxy, n-hexoxy, isohexoxy, and sec-hexoxy.

Specific examples of amide groups suitable for use as an electron donating group include, but are not limited to, acetamide, propanamide, butyramide, isobutyramide, pentanamide, isopentanamide, and tertpentanamide.

Electron withdrawing groups, also referred to as deactivating groups, are groups that remove electron density from the benzene ring. Electron withdrawing groups are typically classified by their strength into groups consisting of strong electron withdrawing groups, moderate electron withdrawing groups, and weak electron withdrawing groups.

Examples of strong electron withdrawing groups include, but are not limited to, a nitro group (—$NO_2$), quaternary amine groups (—$NR_3$), and trihalomethane groups (—$CX_3$). Examples of moderate electron withdrawing groups include, but are not limited to, a cyano group (—C≡N), a sulfonate group (—$SO_3H$), a carboxylic acid group (—COOH), ester groups (—COOR), an aldehyde group (—CHO), and ketone groups (—COR). Examples of weak electron withdrawing groups include, but are not limited to, halogen atoms (—X). For the purpose of defining electron withdrawing groups R can be defined as an alkyl group described above.

Specific examples of ester groups suitable for use as an electron withdrawing group include, but are not limited to, methanoate, ethanoate, propanoate, butanoate, pentanoate, and hexanoate.

Specific examples of ketone groups suitable for use as an electron withdrawing group include, but are not limited to, ethanoyl, propanoyl, butanoyl, pentanoyl, and hexanoyl.

Specific examples of halogen atoms suitable for use as an electron withdrawing group include, but are not limited to, a fluoride atom, a chloride atom, a bromide atom, an iodide atom, and an astatide atom.

As noted above, the Zinhbo derivative may include a chelator group capable of forming a complex with a zinc cation. The chelator group capable of forming a complex with a zinc cation may also be referred to as a zinc-binding ligand. In one or more embodiments, the chelator group capable of forming a complex with a zinc cation include linear or cyclic polyamine chelating groups. Specific examples of groups that form complexes with zinc ions include, but are not limited to, linear polyamine chelators such as di-2-picolylamine, and cyclic polyamine chelators such as 1,4,7,10-tetrazacyclododecane.

In one or more embodiments, 3 of $R^1$, $R^2$, $R^3$, and $R^4$ of formula 1 are hydrogen atoms. In particular embodiments, where $R^1$, $R^3$, and $R^4$ of formula 1 are hydrogen atoms, the Zinhbo derivative may be defined by the following formula 2:

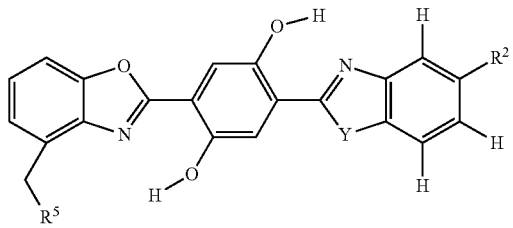

where $R^2$ is an electron withdrawing group or an electron donating group; Y is an oxygen atom, a sulfur atom, a nitrogen atom with a pendant hydrogen atom, or a nitrogen atom with a pendant alkyl group; and $R^5$ is a chelating group attached through a nitrogen atom.

In particular embodiments, where the $R^5$ group of formula 2 is a di-2-picolylamine group, the Zinhbo derivative may be defined by the following formula 3:

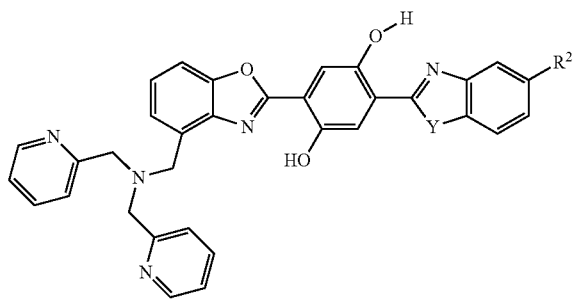

where $R^2$ is an electron withdrawing group or an electron donating group and Y is an oxygen atom, a sulfur atom, a nitrogen atom with a pendant hydrogen atom, or a nitrogen atom with a pendant alkyl group.

Zinhbo derivatives, when excited with an excitation wavelength, will emit one or more fluorescence responses. In one or more embodiments, the uncomplexed Zinhbo derivative, compared to the complexed Zinhbo derivative, has a weak florescence response in the visible region. In one or more embodiments, the Zinhbo derivative complexed with a zinc cation, compared to the uncomplexed Zinhbo derivative, has an increased florescence response in the visible region. In one or more embodiments, the Zinhbo derivative complexed with a zinc cation has florescence response in the near infrared region not detectable in the uncomplexed Zinhbo derivative. In these or other embodiments, the Zinhbo derivative in the presence of zinc cations, compared to the uncomplexed Zinhbo derivative, will produce an increased emission in the visible region, near infrared region, or both the visible and near infrared region.

Zinhbo derivatives when excited with an excitation wavelength will emit one or more fluorescence responses. In one or more embodiments, the uncomplexed Zinhbo derivative will have two florescence response maxima in the visible region. In one or more embodiments, the Zinhbo derivative complexed with a zinc cation has a single florescence response maximum in the visible region. In one or more embodiments, the Zinhbo derivative complexed with a zinc cation has a florescence response maxima in the near infrared region. In these or other embodiments, the Zinhbo derivative in the presence of zinc cations will produce an emission in the visible region, near infrared region, or both the visible and near infrared region.

In one or more embodiments, the Zinhbo derivative may be prepared through a process that comprises preparing a protected compound preparing 2-aminophenol derivative containing a zinc-binding ligand, reacting the protected compound with the 2-aminophenol derivative containing a zinc-binding ligand, and optionally deprotecting the protecting groups.

In one or more embodiments, the protected compound may be defined by the formula:

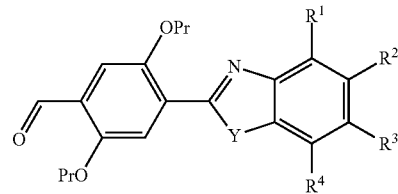

where Y is an oxygen atom, a sulfur atom, a nitrogen atom with a pendant hydrogen atom, or a nitrogen atom with a pendant alkyl group; each Pr is individually a protecting group and $R^1$, $R^2$, $R^3$, and $R^4$ are each individually selected from the group consisting of a hydrogen atom, an electron withdrawing group, and an electron donating group.

Suitable protecting groups include, but are not limited to, alkyl and silyl groups. Specific examples of protecting groups include methyl, ethyl, propyl, butyl, hexyl, methoxymethyl, benzyl, trimethylsilyl, and tert-butyldimethylsilyl groups.

In one or more embodiments, the protected compound may be prepared by reacting a protected dihydroxybenzaldehyde with a hydroxymethyl group with an aminobenzene derivative. The protected compound may be formed when the hydroxyl group of the dihydroxybenzaldehyde with a hydroxymethyl group forms a ring with the amine and a second group on the aminobenzene derivative. The second group on the aminobenzene derivative may be an alcohol, thiol, or a secondary or primary amine. In these or other embodiments, the protected dihydroxybenzaldehyde with a hydroxymethyl group with an aminobenzene derivative are refluxed in ethanol for 0.1 to 10 hours. The crude product is separated from the ethanol, for example, by removing the ethanol under vacuum. The resulting product may then be reacted with pyridinium chlorochromate (PCC) in dichloromethane. The reaction with PCC in dichloromethane may take place in the presence of silica gel.

In one or more embodiments the dihydroxybenzaldehyde with a hydroxymethyl group may be defined by the formula:

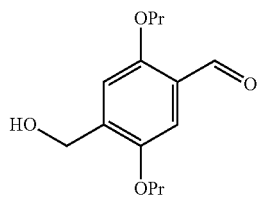

where each Pr is individually a protecting group.

Specific examples of dihydroxybenzaldehydes with a hydroxymethyl group include, but are not limited to, 4-(hydroxymethyl)-2,5-dimethoxybenzaldehyde, 4-(hydroxymethyl)-2,5-diethoxybenzaldehyde, and 4-(hydroxymethyl)-2,5-dihexoxybenzaldehyde.

In one or more embodiments with an aminobenzene derivative defined by the formula:

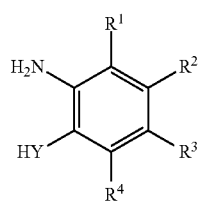

where Y is an oxygen atom, a sulfur atom, a nitrogen atom with a pendant hydrogen atom, and $R^1$, $R^2$, $R^3$, and $R^4$ are each individually selected from the group consisting of a hydrogen atom, an electron withdrawing group, and an electron donating group.

Specific examples of aminobenzene derivatives include, but are not limited to, 2-amino-3-methylphenol, 2-amino-3-methylphenol, 4-tert-butyl-2-aminophenol, and 2-aminophenol.

In one or more embodiments, the 2-aminophenol derivative containing a zinc-binding ligand may be defined by the formula:

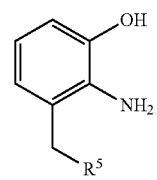

where $R^5$ is a chelating group attached through a nitrogen atom.

Specific examples of 2-aminophenol derivative containing a zinc-binding ligand include, but are not limited to,

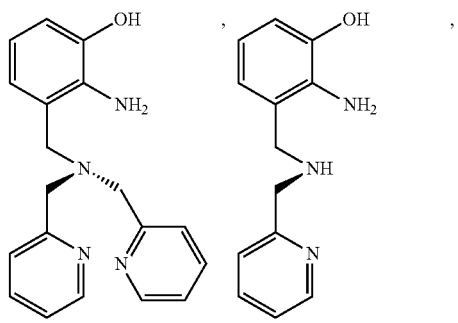

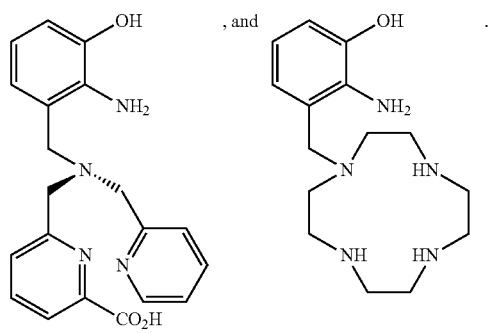

The 2-aminophenol derivative may be produced by different synthetic schemes. The may ultimately be derived from an alkyl 3-alkoxybenzoate such as 2-aminophenol derivative methyl 3-methylbenzoate as shown in the following synthetic scheme, where X is a halogen atom, $R^5$ is a chelating group attached through a nitrogen atom, and $R^6$ is a halogen atom or a tosyl group:

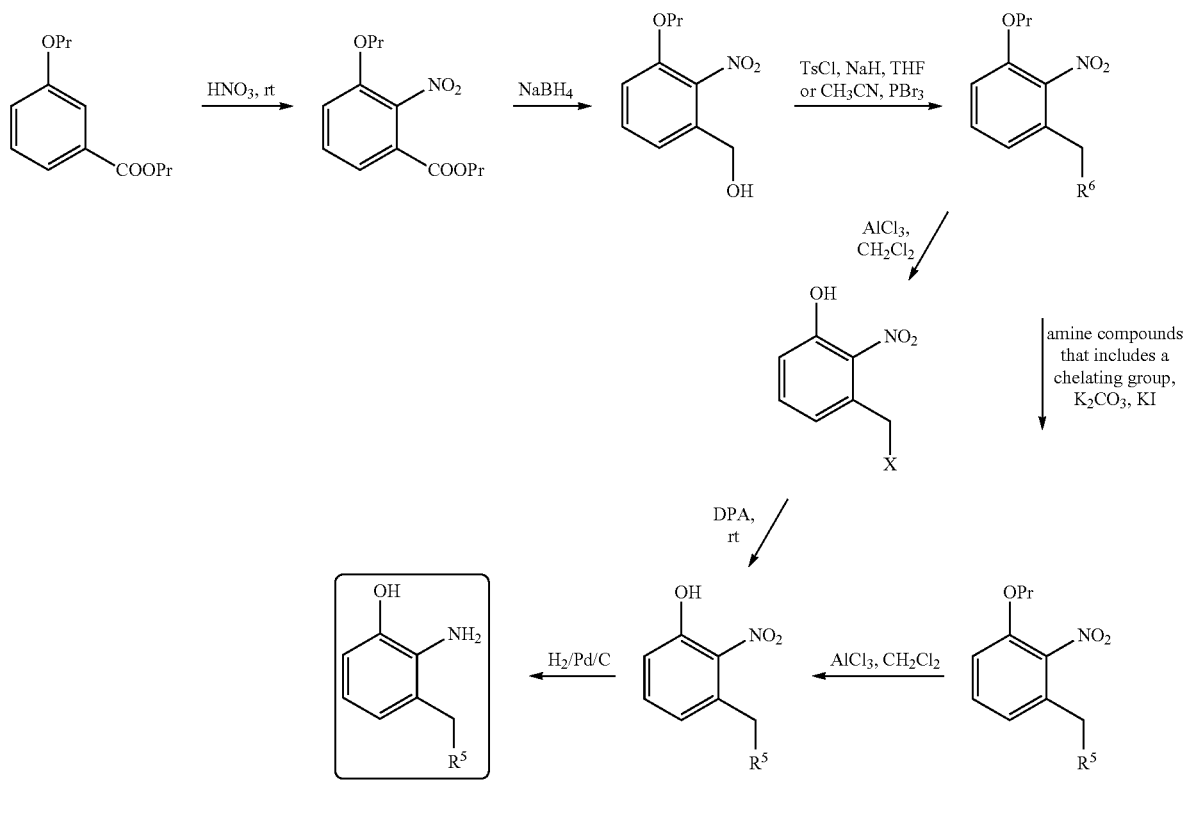

Specific examples of halogen atoms include, but are not limited to, fluoride, chloride, bromide, iodide atom, and astatide.

In one or more embodiments, the 2-aminophenol derivative containing a zinc-binding ligand may prepared by reacting a nitrobenzene derivative defined by the formula

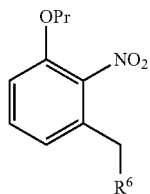

where Pr is a protecting group, and $R^6$ is a halogen atom or a tosyl group, with a amine compound that includes a chelating group; deprotecting the protected oxygen atom; and converting the nitro group to an amine.

Suitable amine compounds that includes a chelating group include, but are not limited to, di-2-picolylamine, 1,4,7,10-tetrazacyclododecane, and pyridin-2-ylmethyl)amine.

In other embodiments, the 2-aminophenol derivative containing a zinc-binding ligand derivative may prepared by reacting a nitrobenzene derivative defined by the formula where Pr is a protecting group, and X is a halogen atom, with a amine compound that includes a chelating group; and converting the nitro group to an amine. For example, the nitrobenzene derivative may be dissolved and reacted with $HNO_3$ (68-70% in aqueous) at room temperature for 2-24 hours, which gives a 2-aminophenol derivative as a precipitate.

As noted above, Zinhbo derivative may be prepared by the reacting the protected compound with the 2-aminophenol derivative containing a zinc-binding ligand. A solution of the protected compound and the 2-aminophenol derivative containing a zinc-binding ligand may be prepared by first dissolving the compounds in dimethylformamide and then further diluting the solution with xylenes. The reaction may be performed by introducing oxygen gas to the protected compound and the 2-aminophenol derivative containing a zinc-binding ligand solution, for example, by bubbling the oxygen gas through the solution. The step of introducing oxygen gas to the solution may be performed in the presence of activated charcoal. The reaction may proceed in the presence of oxygen gas at 110 to 120° C. for about 2 to 4 hr.

After the protected compound and the 2-aminophenol derivative containing a zinc-binding ligand are reacted, any protecting groups may be optionally removed by conventional methods.

In one or more embodiments, the Zinhbo derivative may be prepared through a process that comprises reacting a protected compound with a 2-aminophenol derivative containing a protected alcohol or an alcohol group, converting the protected alcohol or alcohol group to a halogen atom or tosyl group, reacting the halogen atom or tosyl group with a an amine compound that includes a chelating group, and optionally deprotecting any protecting groups.

As noted above, the protected compound may be defined by the formula:

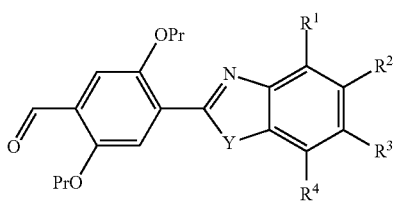

where Y is an oxygen atom, a sulfur atom, a nitrogen atom with a pendant hydrogen atom, or a nitrogen atom with a pendant alkyl group; each Pr is individually a protecting group and $R^1$, $R^2$, $R^3$, and $R^4$ are each individually selected from the group consisting of a hydrogen atom, an electron withdrawing group, and an electron donating group.

In one or more embodiments, the 2-aminophenol derivative containing a protected alcohol or an alcohol group may be defined by the formula

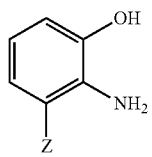

where Z is a carboxylic acid, a protected ester or a hydroxymethyl group. The 2-aminophenol derivative may be produced by different synthetic schemes. The 2-aminophenol derivative may ultimately be derived from an alkyl 3-alkoxybenzoate such as methyl 3-methylbenzoate or alkyl 3-hydroxybenzoate such as methyl 3-hydroxybenzoate as shown in the following synthetic scheme, where $R^7$ is a hydrogen atom or an alkyl group and $R^8$ is an alkyl group In one or more embodiments, the protected compound with a 2-aminophenol derivative containing a protected alcohol or an alcohol group to may be reacted to prepare a molecule defined by the formula I:

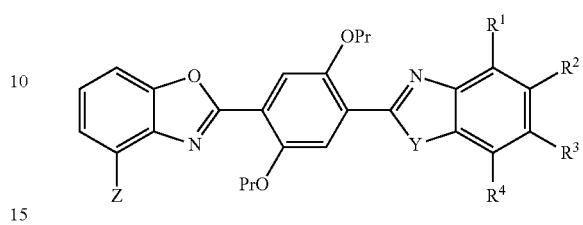

where Z is a carboxylic acid, a protected ester or a hydroxymethyl group: Y is an oxygen atom, a sulfur atom, a nitrogen atom with a pendant hydrogen atom, or a nitrogen atom with a pendant alkyl group; each Pr is individually a protecting group; and $R^1$, $R^2$, $R^3$, and $R^4$ are each individually selected from the group consisting of a hydrogen atom, an electron withdrawing group, and an electron donating group. In one or more embodiments, the process to prepare formula I includes the following: preparing a solution of the protected compound and the 2-aminophenol derivative containing a protected alcohol or an alcohol group may be prepared by first dissolving the compounds in dimethylformamide and then further diluting the solution with xylenes. The reaction may be performed by introducing oxygen gas to the protected compound and the 2-aminophenol derivative containing a protected alcohol or an alcohol group solution, for example, by bubbling the oxygen gas through the solution. The step of introducing oxygen gas to the solution may be performed in the presence of activated charcoal. The reaction may proceed in the presence of oxygen gas at 110 to 120° C. for about 2 to 4 hr.

In one or more embodiments, where the 2-aminophenol derivative containing a protected ester or an alcohol group is a 2-aminophenol derivative containing an alcohol group the 2-aminophenol derivative may be defined by the formula

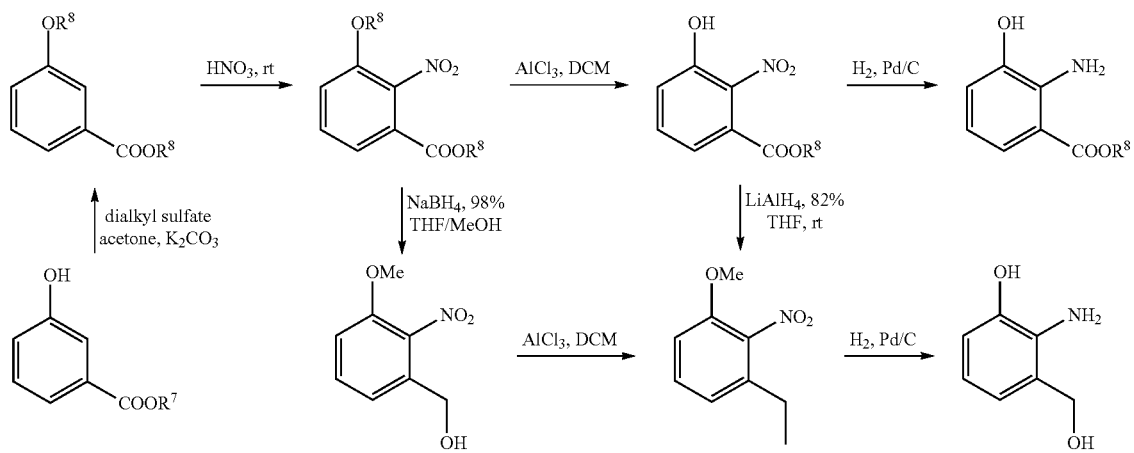

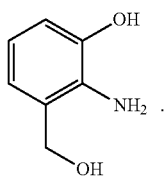

In these or other embodiments, the protected compound and the a 2-aminophenol derivative containing an alcohol group may react to prepare a molecule defined by the formula 2

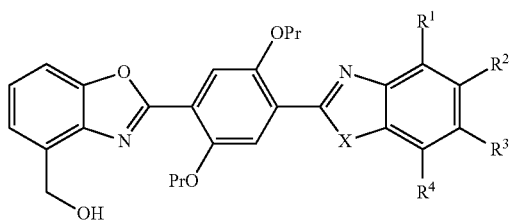

where each Pr is individually a protecting group, Y is an oxygen atom, a sulfur atom, a nitrogen atom with a pendant hydrogen atom, or a nitrogen atom with a pendant alkyl group, and $R^1$, $R^2$, $R^3$, and $R^4$ are each individually selected from the group consisting of a hydrogen atom, an electron withdrawing group, and an electron donating group.

The alcohol group may then be converted to a better leaving group. In one or more embodiments, the alcohol group may be converted to a halogen atom. For example, the hydroxyl group can be converted to bromine atom by reacting $PBr_3$ in acetonitrile at room temperature. In other embodiments, the alcohol group may be converted to a tosylate group by reacting the alcohol with 4-toluenesulfonyl chloride.

In one or more embodiments, where the 2-aminophenol derivative containing a protected ester or an alcohol group is a 2-aminophenol derivative containing a protected ester group the 2-aminophenol derivative may be defined by the formula

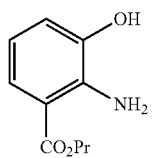

where Pr is a protecting group.

In these or other embodiments, the protected compound and the a 2-aminophenol derivative containing an protected ester group may react to prepare a molecule defined by the formula

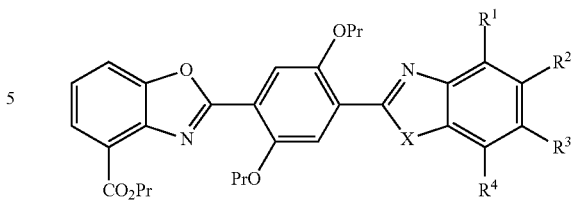

where each Pr is individually a protecting group Y is an oxygen atom, a sulfur atom, a nitrogen atom with a pendant hydrogen atom, or a nitrogen atom with a pendant alkyl group, and $R^1$, $R^2$, $R^3$, and $R^4$ are each individually selected from the group consisting of a hydrogen atom, an electron withdrawing group, and an electron donating group.

The protected ester may then be converted to a leaving group. In one or more embodiments, the protected ester group may be converted to a hydroxymethyl group, and then to a halogen-substituted methyl. In a typical procedure, the ester group can be converted to hydroxymethyl group by heating the ester with sodium boronhydride to reflux in dry THF solvent until the reaction is complete. The progress of reaction may monitored by thin layer chromatography. The hydroxymethyl group can then be converted to bromomethyl group by reacting with $PBr_3$ in acetonitrile at room temperature. In other embodiments, the protected ester group may be converted to hydroxymethyl group, which can then be converted to a tosylate group. For example, reaction of the hydroxymethyl group with 4-toluenesulfonyl chloride can give the desired tosylate in THF at room temperature.

Regardless of if the leaving group is a tosyl or halogen atom, the leaving group may be reacted with an amine compound that includes a chelating group.

After the leaving group is reacted with an amine compound any protecting groups may be optionally removed by conventional methods.

In one or more embodiments, the Zinhbo derivatives may be used to detect the presence of zinc cations in a test sample. The test sample is a substance that may contain zinc ions. The Zinhbo derivative is contacted with the test sample. An excitation wavelength is then applied to the test sample. In the presence of zinc cations a Zinhbo derivative will form a complex with a zinc ion and the Zinhbo derivative will give an emission wavelength or florescence response that corresponds to complexed Zinhbo derivative, thus indicating the presence of zinc cations in the test sample. In the absence of zinc cations, the Zinhbo derivative will not form a complex and the Zinhbo derivative will give an emission wavelength corresponding to uncomplexed Zinhbo derivatives.

The test sample may be obtained directly from a source to be tested for the presence of zinc cations, or it may be created by dissolving or diluting a source to be tested for the presence of zinc cations.

In one or more embodiments, solvents suitable for the creation of test samples include solvents selected from the group consisting of aqueous solvents, protic solvents, and organic solvents. Examples of aqueous solvents include, but are not limited to, water and pH buffered solutions. Examples of protic solvents include, but are not limited to, lower alcohols, such as methanol and ethanol. Examples of organic solvents include, but are not limited to, tetrahydrofuran and methylene chloride.

As a unique feature, the Zinhbo derivative give two emission signals upon binding to zinc cations; one emission in the visible region, and the other emission signal in the near infrared region. One advantage of this method is that it can be used to test a large number of test samples all at the same time. This is shown in FIG. 1, showing a method 10, wherein a light source 12 directs light 30 (a stimulated emission of photons) through a first container 14 holding a test sample 16, a second container 18 holding a test sample 20 and a third container 22 holding a test sample 24. As seen, the first container 14 and third container 28 hold test samples 16 that include zinc, because the light 30 causes fluorescence whose color can be seen visually as at 26 (container 14) and 28 (container 22). The second container 18 does not show fluorescence and thus, the test sample 20 placed therein does not include zinc. Although the response of the colored fluorescence signal can be detected visually by the naked eye, the signals in the near infrared region can give more sensitive detection.

In one or more embodiments, the Zinhbo derivative may be used to detect the presence of zinc cations in vivo. The presence of zinc cations in vivo by testing an entire living organism or a portion of an organism that contains living cells for the presence of zinc cations.

The Zinhbo derivative may be added in vivo, by contacting living cells with a Zinhbo derivative. In one or more embodiments, the living cells that are contacted by the Zinhbo derivative are tissues or part of a living organism. Examples of methods of contacting living cells with a Zinhbo derivative include, but are not limited to, incubating cultured cells with the Zinhbo derivative in a culture medium, injecting Zinhbo derivative into living cells. Examples of methods of contacting a living organism with a Zinhbo derivative include, but are not limited to, treating a portion of water containing an aquatic animal with a Zinhbo derivative. Other methods of contacting a living organism with a Zinhbo derivative include, but are not limited, having the living organism ingest the Zinhbo derivative and injecting the Zinhbo derivative into the living organism.

In one or more embodiment, the presence of zinc cations in vivo may be found by exciting the living cells or living organism with an excitation wavelength. If zinc ions are present in vivo the Zinhbo derivative will form a complex with a zinc ion and the Zinhbo derivative will give an emission wavelength, or florescence response, corresponding to complexed Zinhbo derivatives and the presence of zinc cations will be detected. In the absence of zinc cations, the Zinhbo derivative will not form a complex and the Zinhbo derivative will give an emission wavelength corresponding to uncomplexed Zinhbo derivatives.

In one or more embodiments, the Zinhbo derivative may be used to detect the presence of free zinc cations in vivo. Free zinc cations refer to the unbound zinc cations in a cell. Zinc in a cell may be bound to proteins. Zinc imbalance in certain tissues is found to be associated with several chronic diseases such as diabetes and Alzheimer's disease. Examples of tissues where free zinc cations may be found includes, but is not limited to, brain, insulin, intestine, and retina.

In particular embodiments, when the Zinhbo derivative is used to detect the presence of zinc cations or free zinc cations in vivo, it is beneficial to detect the response emission in the near infrared wavelengths. Detection in the near infrared wavelengths is advantageous because wavelengths in the near infrared region can penetrate deeper into biological tissues. In some embodiments, wavelengths in the infrared region can penetrate up to about 4 cm of biological tissue. In some embodiments, wavelengths in the infrared region can penetrate up to about 3 cm of biological tissue.

In one or more embodiments, the Zinhbo derivative may be used to detect zinc cations in an organism by scanning an organism with a near infrared light.

The ability of wavelengths in the infrared region to penetrate biological tissue allows for Zinhbo derivatives to be used to scan an organism for zinc or free zinc cations. In one or more embodiments, an entire organism can be scanned for the presence of zinc cations by delivering a Zinhbo derivative internally to an organism, exciting the entire organism with an excitation wavelength, and detecting the florescence response emission. In one or more embodiments, a portion organism can be scanned for the presence of zinc cations by delivering a Zinhbo derivative internally to an organism, exciting a portion of the organism with an excitation wavelength, and detecting the florescence response emission. By scanning an organism or a portion of an organism for zinc cations it allows a map of zinc content within the organism to be determined which may benefit in the treating and research of diseases associated with the imbalance of zinc with in the organism's tissues, such as cancer, diabetes and Alzheimer's disease.

The amount of Zinhbo derivative used to detect zinc ions can also be defined in terms of nM. In one or more embodiments, the amount of Zinhbo derivative in solution is 0.01 nM to 100 nM. In other embodiments, the amount of Zinhbo derivative in solution is 0.1 nM to 50 nM. In still other embodiments, the amount of Zinhbo derivative in solution is 0.2 nM to 5 nM.

In one or more embodiments, the Zinhbo derivatives are excited with an excitation wavelength from about 400 nm to about 550 nm. In one or more embodiments, the Zinhbo derivatives are excited with an excitation wavelength from about 430 nm to about 500 nm. In particular embodiment, the Zinhbo derivatives are excited with an excitation wavelength at about 480 nm.

In one or more embodiments, the Zinhbo derivative complexed with a zinc cation has a florescence response emission in the near infrared region. In one or more embodiments, the Zinhbo derivative has a florescence response emission in the range of about 700 to about 900 nm. In one or more embodiments, the Zinhbo derivative has a florescence response emission in the range of about 710 to about 800 nm. In these or other embodiments the Zinhbo derivative has a florescence response emission at about 760 nm.

In one or more embodiments, the Zinhbo derivative complexed with a zinc cation has an increased florescence response emission in the visible region. In one or more embodiments, the Zinhbo derivative has a florescence response emission in the range of about 500 nm to about 700 nm. In one or more embodiments, the Zinhbo derivative has a florescence response emission in the range of about 530 nm to about 590 nm. In these or other embodiments the Zinhbo derivative has a florescence response emission at about 550 nm.

In one or more embodiments, the Zinhbo derivative will exhibit a fluorescence response emission when excited in the visible region. In these and other embodiments, the Zinhbo derivative complexed with a zinc cation have two or more florescence response emissions in the range of about 500 nm to about 900 nm. In these embodiments, the presence of zinc cations can be detected by emissions in the visible region, near infrared region, or both the visible and near infrared region.

In one or more embodiments, the uncomplexed Zinhbo derivative has a florescence response emission when excited in the range of about 400 to about 700 nm. In other embodiments, the uncomplexed Zinhbo derivative has a florescence response emission when excited in the range of about 510 to about 570 nm. In one or more embodiments, the uncomplexed Zinhbo derivative has two florescence response emission maxima in the range of about 510 to about 570 nm. In these or other embodiments the Zinhbo derivative has a florescence response emission at about 520 nm and a florescence response emission at about 560 nm.

In light of the foregoing, it should be appreciated that the present invention significantly advances the art by providing Zinhbo derivatives and processes for preparing Zinhbo derivatives that are improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Synthetic design I

In the new experiment design, the strategy for the synthesis of bis(HBO) derivatives is based on a retrosynthetic analysis involving the bond disconnections shown in Scheme 1. The synthetic direction was proposed as follows: (1) preparation of the key intermediate A, which incorporates the DPA group in the early stage; (2) efficient synthesis of benzoxazole B from aldehyde C and 2-amino-phenol D; (3) reaction of A and B to give the bis(HBO) products.

Scheme 1. Retrosynthetic analysis of Bis-HBO derivatives.

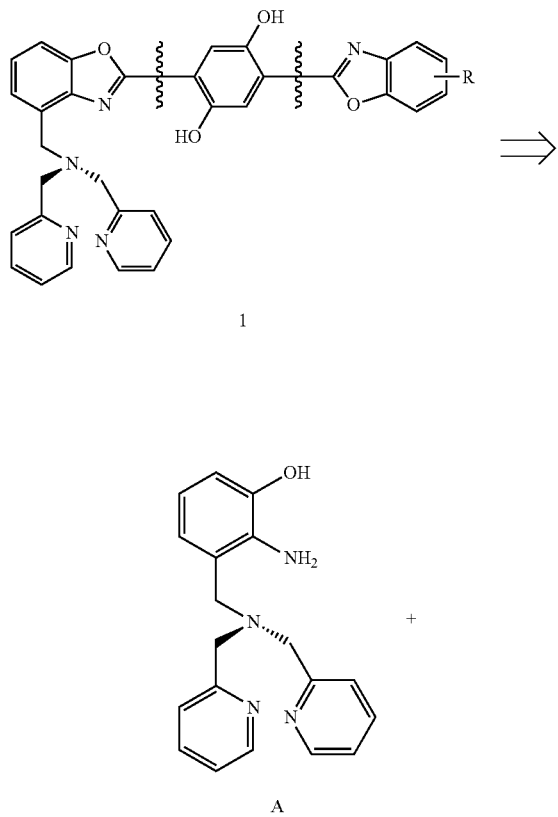

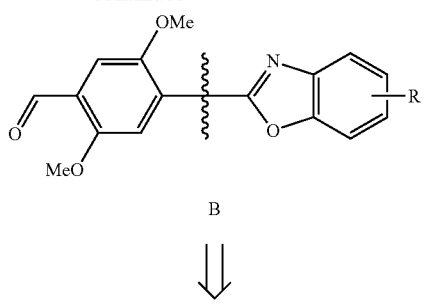

B

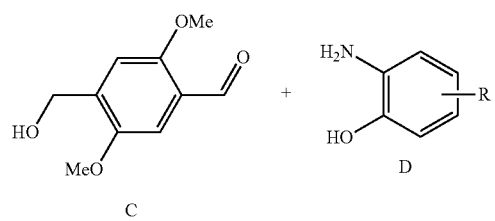

C

Scheme 2 presents the construction of the requisite key intermediate A. Thus compound 5 was prepared conveniently by the nitration of 4 with nitric acid at room temperature, which precipitated from the solution and was recrystallized from EtOAc/hexane as large colorless crystals (50-60% yield). Selective reduction of ester 5 by $NaBH_4$ in THF/MeOH proceeded cleanly to furnish alcohol 6, which then underwent tosylation or bromination to provide corresponding 7 or 8 in almost quantitative yields. Reaction of 7 or 8 with 2,2'-dipicolylamine (DPA) in the presence of $K_2CO_3$ and KI gave compound 9 in good yields. Deprotection of the methoxy group proceeded smoothly at room temperature by using $AlCl_3$ to give 10, which was then reduced by $H_2$ over Pd/C to afford the intermediate A in almost quantitative yield. Although the procedure was quite satisfactory on a small scale (e.g., 1 mmol), the deprotection of 9 by $AlCl_3$ was found to be troublesome for a larger scale reaction (e.g., 5 mmol). The reaction was not complete even when using a large excess of $AlCl_3$. This is because some syrup-like residue precipitated out during the reaction, possibly due to (a) chelation of $AlCl_3$ with DPA, and (b) encapsulation of unreacted 9. In order to overcome the deficiency in the deprotection of 9, our attention was directed to seek deprotection of the methyl phenol ether at an earlier stage, i.e. before introduction of DPA. Attempts to deprotect the methyl from the phenol ether 6 gave low yield by using either $AlCl_3$ or $BBr_3$. However, the methyl group of 8 was removed effectively by using $AlCl_3$ to give 3-(bromomethyl)-2-nitrophenol, which could be converted to 10 in high yield.

Scheme 2. Synthesis of key intermediate A.
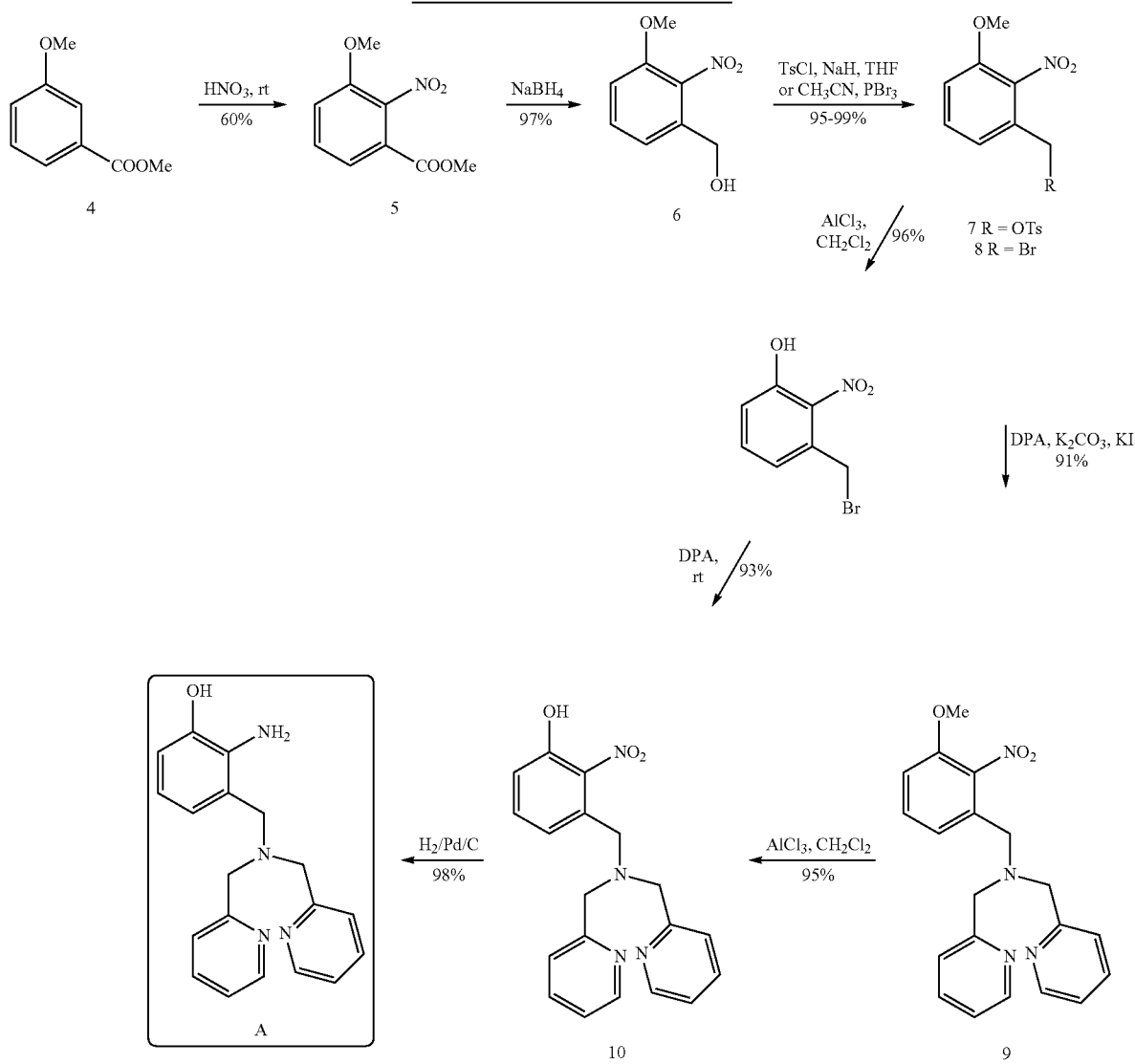
Scheme 3. Synthesis of key intermediate B.
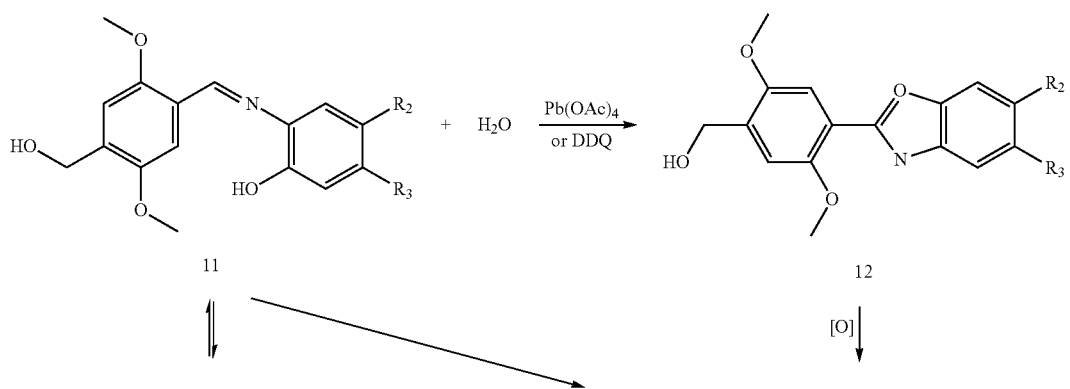

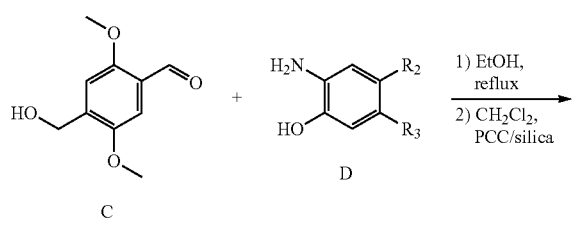
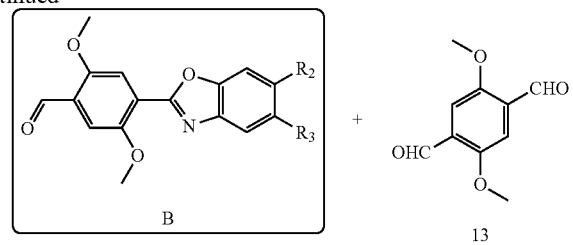

b: $R_2$ = t-Bu, $R_3$ = H; c: $R_2$ = $R_3$ = H; d: $R_2$ = H, $R_3$ = $CH_3$;

The next step was to find an efficient reaction sequence to construct the benzoxazole fragment B from intermediate C and 2-aminophenols D (Scheme 3). In the synthesis of benzoxazole compounds, most reported methods require the isolation of the initial product imine 11, followed by an oxidative cyclization to form the benzoxazole intermediate 12. Although DDQ and Pb(OAc)$_4$ worked well for oxidative cyclization of 11, the reaction typically gave the alcohol 12 without further oxidation. An additional oxidation step is thus required to further oxidize the alcohol to give aldehyde B. An intriguing question is whether one can find a suitable oxidant that can execute both "oxidative cyclization" and "oxidation of alcohol to aldehyde", thereby greatly simplifying the reaction procedure. Bearing this in mind, we decided to examine PCC which is known to oxidize primary alcohols to aldehydes and to oxidize imine to benzoxazoles as well. Simple mixing of C and D with PCC in $CH_2Cl_2$ led to B in 26% yield, and a large amount of byproduct was identified as 13. The initial result indicated that PCC was effective for both cyclization and oxidation. Interestingly, during TLC monitoring of the reaction, we found C and D reacted quickly on TLC plate, forming imine intermediate 11. The observation encouraged us to optimize the reaction conditions with silica gel and PCC. After extensive trials, a one-pot multistep method for the synthesis of B (by direct reaction between C and D) was developed in 60% yield with high reproducibility by silica gel and PCC.

Scheme 4. Construction of Bis(HBO) system.

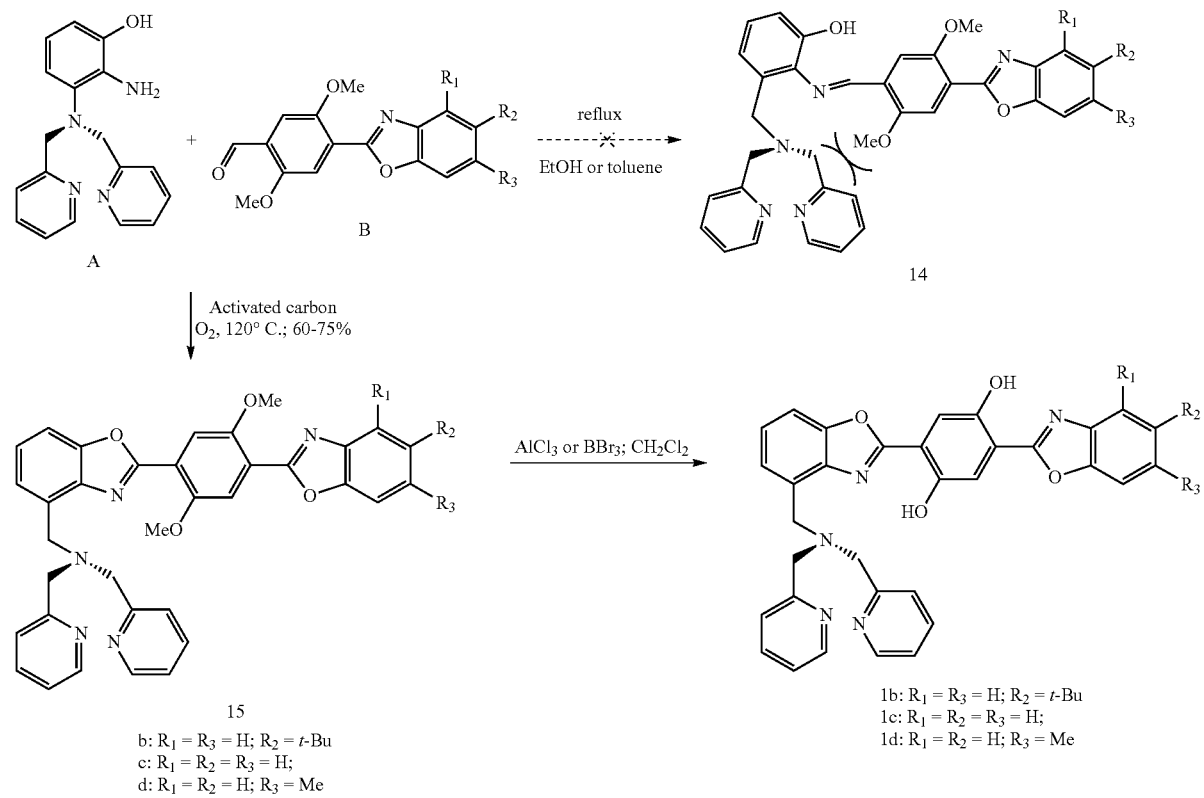

1b: $R_1$ = $R_3$ = H; $R_2$ = t-Bu
1c: $R_1$ = $R_2$ = $R_3$ = H;
1d: $R_1$ = $R_2$ = H; $R_3$ = Me

Finally, the coupling of A and B was studied (Scheme 4). Unfortunately, all the reported catalysts and reagents such as Mn(OAc)$_3$, KAl(SO$_4$)$_2$, Pb(OAc)$_4$, Ba(MnO$_4$)$_2$, DDQ and even the PCC/silica gel method failed to give any desirable 15 (Scheme 4). It was found that the imine 14 was not formed by refluxing A and B in EtOH or toluene overnight, probably due to the steric hindrance. After exhaustive exploration, fortunately, we found that Tagawa's method by $O_2$ with activated carbon gave 15 in up to 72% yield. The final product 1b could be easily prepared by the deprotection of methoxy groups catalyzed by $AlCl_3$ or $BBr_3$ in anhydrous $CH_2Cl_2$. With the availability of the intermediate A, the products could be effectively synthesized in 2 steps in high yields (1b-1d).

In summary, an efficient method has been developed for the synthesis of bis(HBO) system with the zinc-chelating DPA functionality. When used together with silica gel, PCC was found to be effective for both "oxidative cyclization" and "oxidation of alcohol," thereby greatly simplifying the reaction sequence. Since the bis(HBO) sensor 1 has attractive characteristics for zinc detection such as large Stokes shift and NIR emission, our new synthetic method for 1 thus makes this material accessible for use in relevant fields. In addition, the developed methodology could be used for synthesis of a wide range of new benzoxazole-containing materials for their property studies.

Synthesis of 5. 3-Hydroxybenzoic acid (Acros) (1.38 g) was dissolved in acetone (40 mL), then $K_2CO_3$ (3.0 g) and dimethyl sulfate (2.7 g) were added in one portion. The mixture was heated to reflux under stirring for 1-2 hours until 3-hydroxybenzoic acid was completely consumed to form 4 (monitored by TLC). Then the reaction mixture was cooled down to room temperature, and filtered through a short pad of silica gel to remove $K_2CO_3$. The resulting solid residue was washed with acetone (200 mL). The clear filtration was concentrated under vacuum to give a syrup-like residue, which was dissolved in 15 mL $HNO_3$ (68-70% in aqueous as received) at room temperature. The solution was well stirred overnight until the starting material was consumed (monitored by TLC). Compound 5 was precipitated out from the solution (nitration by-products 5a and 5b were still in the solution and were recovered by extraction with $CH_2Cl_2$). Simple filtration will afford 5, which was recrystallized from MeOH or EtOAc/Hexane to give large colorless square crystals as pure product in about 50-60% yield. $^1$H NMR (300 MHz, $CDCl_3$): 7.58 (1H, dd, J=1.2 Hz, J=7.2 Hz), 7.47 (1H, tri, J=8.1 Hz), 7.24 (1H, dd, J=1.2 Hz, J=8.1 Hz), 3.90 (3H, s), 3.87 (3H, s). $^{13}$C NMR (75 MHz, $CDCl_3$): 163.4, 150.9, 130.8, 123.6, 122.1, 117.1, 56.8, 52.9.

General procedure for synthesis of intermediate B. Intermediate compounds C (600 mg) and D (3.2 mmol) were dissolved in EtOH (50 mL), and the mixture was refluxed overnight. The crude product mixture was concentrated under vacuum and dried in a vacuum oven overnight. The resulting mixture was then re-dissolved in 80 mL anhydrous $CH_2Cl_2$ (Solution I). PCC (1.5 g) and silica gel (4.5 g) were mixed in 80 mL $CH_2Cl_2$ and stirred at room temperature for one hour (Solution II). The PCC solution II was added to the solution I and the mixture was stirred overnight and then filtered through a short pad of silica and washed by EtOAc. The organic phase was collected, concentrated in vacuum, and purified on a silica gel column to give B in 50-65% yield as yellow solid. Compound Bb was synthesized by reaction of the aldehyde C with 2-amino-4-(tert-butyl)phenol. $^1$H NMR (300 MHz, $CDCl_3$): 10.50 (1H, s), 7.87 (1H, d, J=1.2 Hz), 7.80 (1H, s), 7.53 (1H, d, J=8.4 Hz), 7.52 (1H, s), 7.45 (1H, dd, J=1.2 Hz, J=8.4 Hz), 4.01 (6H, s), 1.39 (9H, s). $^{13}$C NMR (75 MHz, $CDCl_3$): 189.2, 160.8, 155.9, 152.7, 148.9, 148.5, 142.0, 126.9, 123.8, 122.8, 117.2, 114.7, 111.3, 110.1, 57.0, 56.6, 35.2, 31.9.

General procedure for synthesis of 15. Intermediate compounds A (1.0 mmol) and B (2-3 mmol) were dissolved in DMF (1 mL), and the solution was subsequently diluted with xylenes to 30 mL. After addition of activated carbon (100-200 mg), the mixture was well stirred at 110-120° C. while oxygen gas was bubbled into the reaction mixture. Upon completion of the reaction, the mixture was filtered and washed by EtOH. The resulting crude product was concentrated and purified on a silica gel column to give 15 in 60-75% yields. Compound 15b. $^1$H NMR (300 MHz, $CDCl_3$): 8.44 (2H, d, J=4.5 Hz), 7.82 (3H, d, J=6.6 Hz), 7.71 (1H, d, J=8.1 Hz), 7.57 (2H, td, J=1.5 Hz, J=7.5 Hz), 7.51 (1H, d, J=7.5 Hz), 7.45 (1H, d, J=7.8 Hz), 7.38 (1H, dd, J=1.8 Hz, J=8.7 Hz), 7.30 (1H, tri, J=7.8 Hz), 7.07-7.02 (2H, m), 4.19 (2H, s), 4.04 (3H, s), 4.01 (3H, s), 3.89 (4H, s), 1.33 (9H, s). $^{13}$C NMR (75 MHz, $CDCl_3$): 160.7, 160.3, 152.6, 152.6, 150.9, 149.2, 148.8, 148.4, 142.1, 141.4, 136.6, 131.6, 125.4, 124.8, 123.5, 122.9, 122.1, 119.9, 119.8, 117.1, 115.5, 115.2, 109.9, 109.5, 60.6, 57.3, 57.3, 53.7, 35.2, 32.0, 29.9, 29.6.

Synthesis of 1b. Compound 15b (300 mg) was dissolved in anhydrous $CH_2Cl_2$, and the solution was cooled to −78° C. Then $BBr_3$ (800 mg) or $AlCl_3$ (400 mg) was added slowly, and the resulting mixture was warmed to room temperature and stirred overnight. Then the reaction mixture was quenched by addition of water, and $CH_2Cl_2$ layer was separated on a silica gel column in 78% yield. $^1$H NMR (300 MHz, $CDCl_3$): 11.04 (1H, d, J=1.2 Hz), 11.01 (1H, s), 8.53 (2H, tri, J=1.2 Hz), 7.80 (3H, m), 7.72-7.62 (4H, m), 7.58-7.48 (4H, m), 7.40 (1H, tri, J=7.8 Hz), 7.15 (2H, m), 4.15 (2H, s), 3.91 (4H, d, J=1.5 Hz), 1.42 (9H, tri, J=1.2 Hz). $^{13}$C NMR (75 MHz, $CDCl_3$): 161.9, 161.6, 159.6, 151.1, 150.9, 149.3, 149.0, 147.4, 140.0, 139.5, 136.6, 130.6, 126.1, 125.8, 123.9, 122.8, 122.0, 116.1, 114.9, 114.5, 110.0, 109.6, 60.4, 53.7, 35.1, 31.8.

Synthetic Design II

This synthetic design is based on the following knowledge: (a) bromination and tosylation of benzylic hydroxyl group can be accomplished in more than 90% yields; (b) replacement of Br or OTS by the chelating group, such as DPA has also been reported in up to 99% yield as well. As shown in Scheme 5, the efficient synthesis is dependent on the construction of key intermediate 4, which could be obtained by reduction of ester 5 or directly coupling between 8 and 7.

Scheme 5 Synthetic design for bis(HBO).

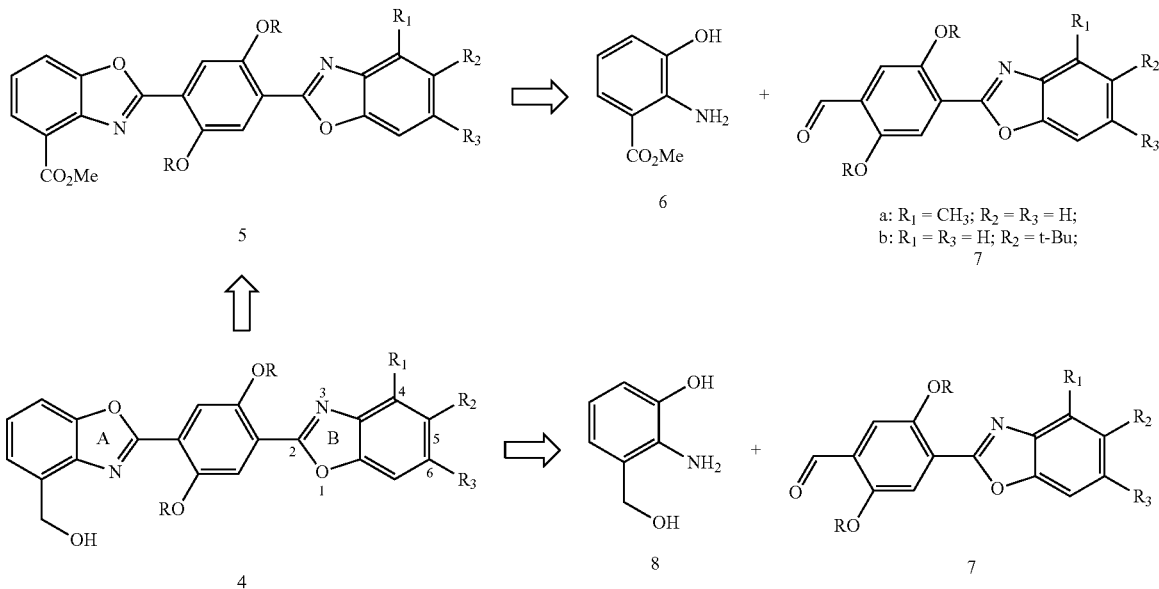

a: $R_1 = CH_3$; $R_2 = R_3 = H$;
b: $R_1 = R_3 = H$; $R_2 = t$-Bu;

Our initial attention was directed to the synthesis of 2-aminophenol derivatives 6 or 8. First, nitration of 9 with nitric acid failed to produce the desired nitro compound such as 12 in a reasonable yield, because the nitration of phenol led to a mixture of nitro products as precipitation, which were hard to separate from each other. Therefore, the phenol of the methoxyl group was successful with $AlCl_3$ in DCM to give 12 in almost quantitative yield, and the deprotection could be carried out in gram scales. In addition, selective reduction of the nitro group by Pd/C gave the desirable 6 in quantitative yield.

Scheme 6 Synthesis of the key intermediates 6 and 8.

9 was converted to 10, which could be totally dissolved in nitric acid solution. Interestingly, the nitro compound II precipitated out as white solid, which could be easily separated from the other nitro by-products by filtration. The nitro compound II could be further purified by recrystallization in MeOH or EtOAc/Hexane to give large colorless square crystals as pure product in about 50-60% yield. Deprotection Our next target was the synthesis of 2-aminophenol derivative 8, which was desirable for the construction of 4 (Scheme 5). Selective reduction of the carboxyl ester 11 by $LiAlH_4$ in dry THF or $NaBH_4$ in THF/MeOH gave 13 in up to 92-98% yield (Scheme 6). The deprotection of methoxyl group of 13 by $AlCl_3$, however, gave 14 in only 61% yield, along with some unreacted 13. Although the deprotection of 13 by $BBr_3$ also gave 14, the reaction mixture contained several unidentified by-products. Selective reduction of ester 12 by $NaBH_4$ in THF/MeOH even did not proceed. We finally found 12 could be reduced by $LiAlH_4$ in anhydrous THF to afford 14 in about 82% yield. Then the desirable 8 was prepared by hydrogenation catalyzed by Pd/C.

With the convenient synthesis of 2-aminophenol derivatives 6 and 8, our next attention then turned to the construction of the benzoxazole "A" from aminophenol 6 (or 8) and aldehyde 7b. To our surprise, the reported catalysts and methods, such as $Mn(OAc)_3$, $KAl(SO_4)_2$, $Pb(OAc)_4$, $Ba(MnO_4)_2$, and DDQ did not work in this case at all. When the reaction of 6 and 7b was monitored carefully by TLC, we found that the imine intermediate I was not formed after the reaction mixture was refluxed in EtOH or toluene overnight. A likely reason was due to the large steric hinderance. After exhaustive exploration, we were happy to find that Y. Tagawa's method by $O_2$ with activated carbon worked very well in this case, resulting in the bis(HBO) 5b in as high as 78% yield. The coupling of 8 and 7b was carried out with Y. Tagawa's method as well, however it only gave 4b in 42% yield. Thus, the reaction of 6 and 7 was adopted to obtain the key intermediate 5.

Scheme 7 Construction of the benzoxazole A.

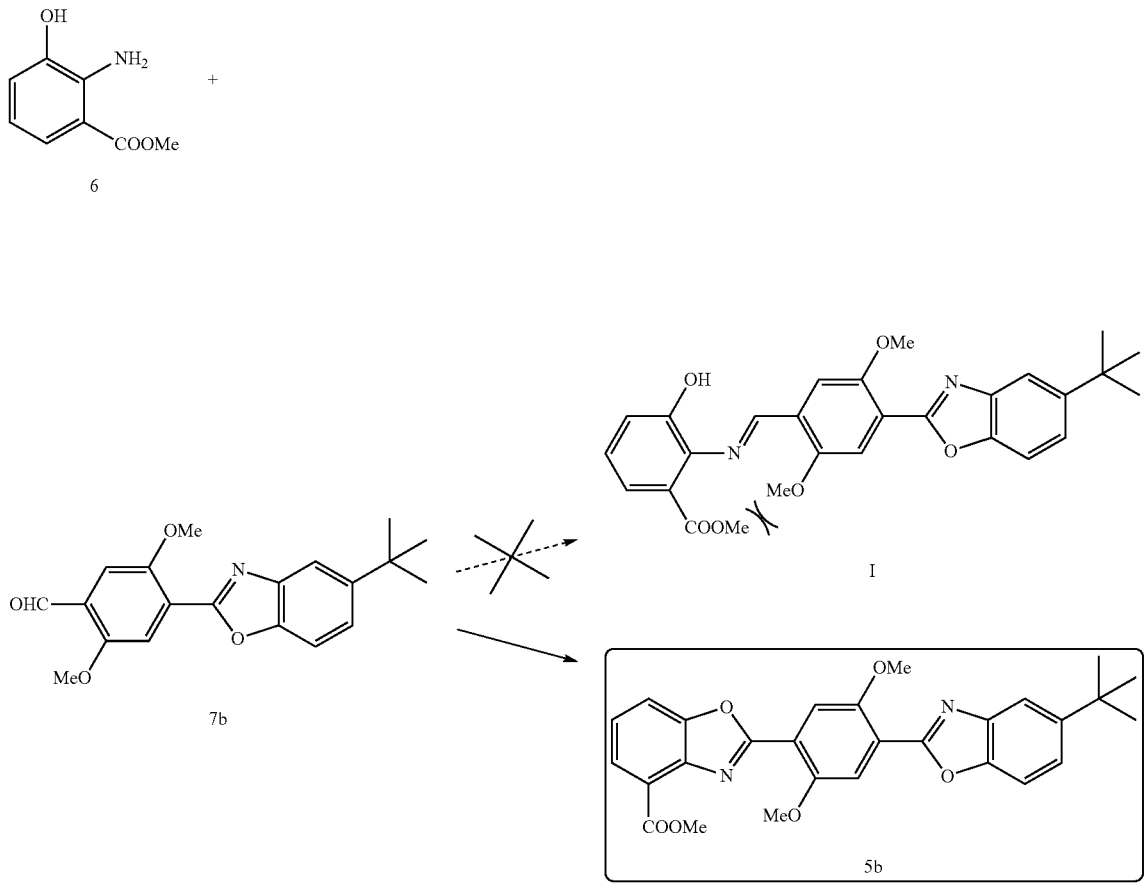

Scheme 8 Reduction of the carboxylic ester.

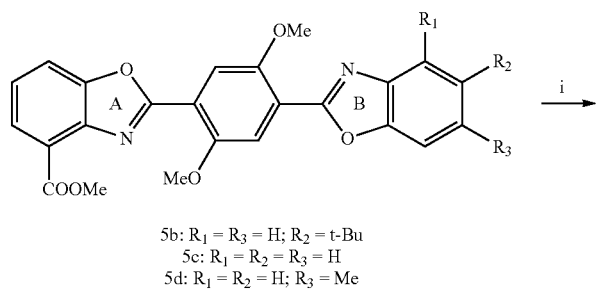

5b: $R_1 = R_3 = H$; $R_2 = t$-Bu
5c: $R_1 = R_2 = R_3 = H$
5d: $R_1 = R_2 = H$; $R_3 = Me$

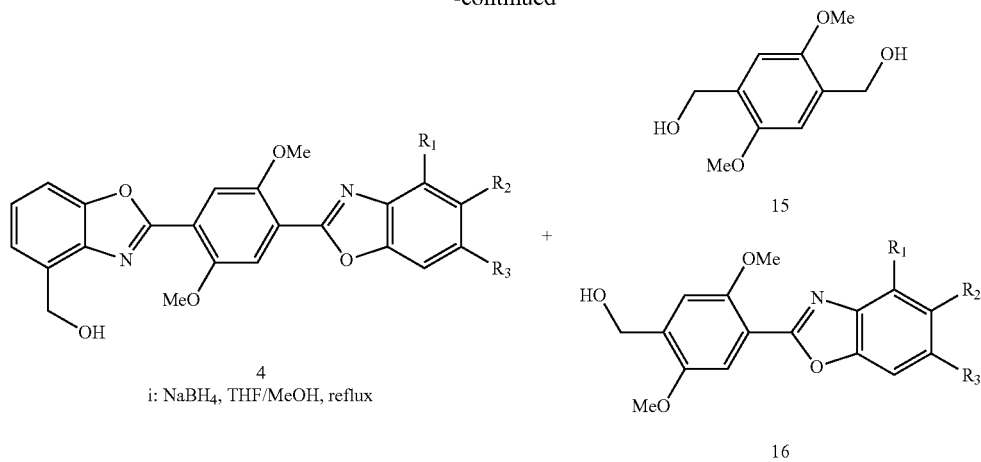

4
i: NaBH₄, THF/MeOH, reflux

15

16

Reduction of the carboxylic ester group of 5 was then studied with different methods. Though LiAlH₄ is well-known to be an efficient reducing reagent for esters, however both benzoxazole rings A and B could not survive the harsh reaction conditions, resulting in the separation of compound 15 as the major product. What is more, reduction by NaBH₄ in MeOH also resulted in partial decomposition of the benzoxyl rings as well, such as a small amount of 16 was observed in the reaction. Finally, we found in anhydrous THF with NaBH₄, both benzoxyl rings were stable even under reflux conditions. Careful reduction by NaBH₄ in THF and treated by MeOH at the end of the reaction resulted in 82-88% yield of compound 4.

Scheme 9 Transformation of the benzylic hydroxyl group to better leaving groups.

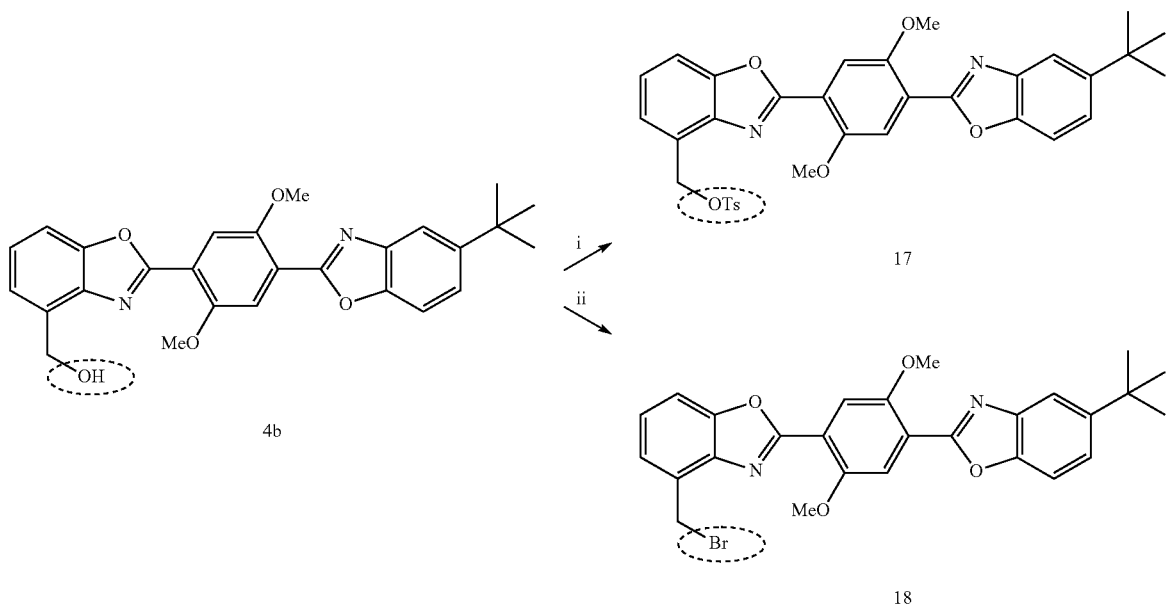

i: NaH, THF, rt, 30% yield; ii: PBr₃, CH₃CN, rt, 99% yield.

Scheme 10 Synthesis of bis[2-(2'-hydroxyphenyl)benzoxazole] zinc sensor 2.

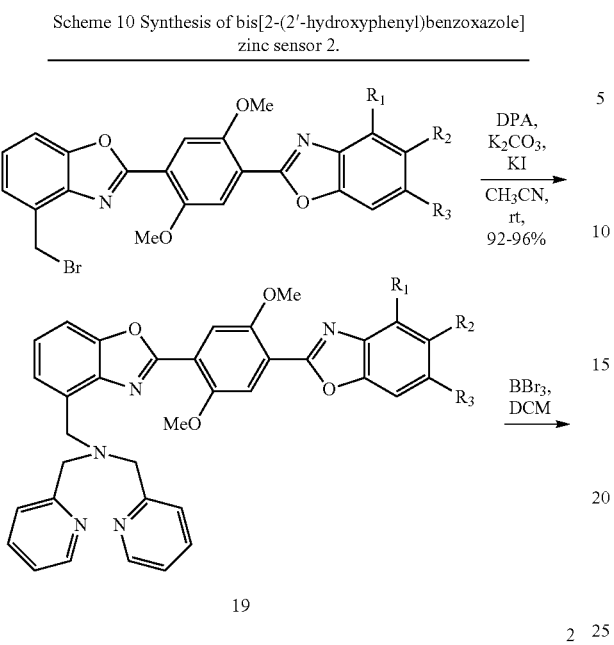

Subsequently, transformation of the benzylic hydroxyl to a better leaving group was studied. By using pyridine, TEA or Na$_2$CO$_3$, the tosylation of 4b did not proceed at all. Treatment of 4b with NaH (a stronger base) in THF, however, led to 17 in only about 30% yield as tosylation product, along with several unidentified byproducts, which makes subsequent purification a very difficult task. The result suggested that the benzoxazole rings were not stable under strong base conditions. Fortunately, bromination of 4 by PBr$_3$ in acetonitrile gave 18 in excellent yield (up to 99%). The replacement of bromide by DPA was also found to proceed smoothly in acetonitrile in the presence of K$_2$CO$_3$ at room temperature (1-2 hours). And the deprotection of the methoxyl group with BBr$_3$ was successful as reported to give the final products 2.

What is claimed is:

1. A process of preparing a Zinhbo derivative comprising:
(i) reacting a protected compound defined by the formula:

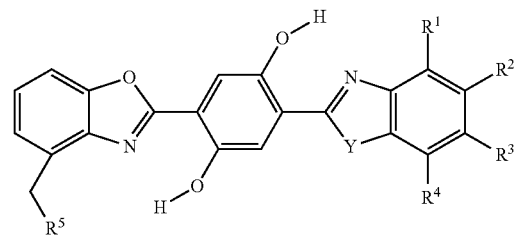

where Y is an oxygen atom, a sulfur atom, a nitrogen atom with a pendant hydrogen atom, or a nitrogen atom with a pendant alkyl group; each Pr is individually a protecting group and R$^1$, R$^2$, R$^3$, and R$^4$ are each individually selected from the group consisting of a hydrogen atom, an electron withdrawing group, and an electron donating group;
with a the 2-aminophenol derivative defined by the formula

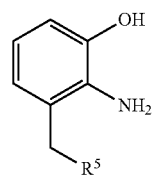

where R$^5$ is a chelating group attached through a nitrogen atom, via a process that includes an oxidation reaction; and (ii) deprotecting the protecting groups to form a Zinhbo derivation defined by the following formula:

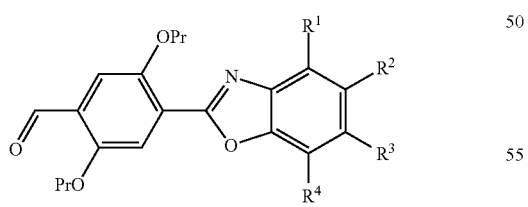

where R$^1$, R$^2$, R$^3$, and R$^4$ are each individually selected from the group consisting of a hydrogen atom, an electron withdrawing group, and an electron donating group; Y is an oxygen atom, a sulfur atom, a nitrogen atom with a pendant hydrogen atom, or a nitrogen atom with a pendant alkyl group; and R$^5$ is a chelating group attached through a nitrogen atom.

2. The method of claim 1, where the 2-aminophenol is selected from

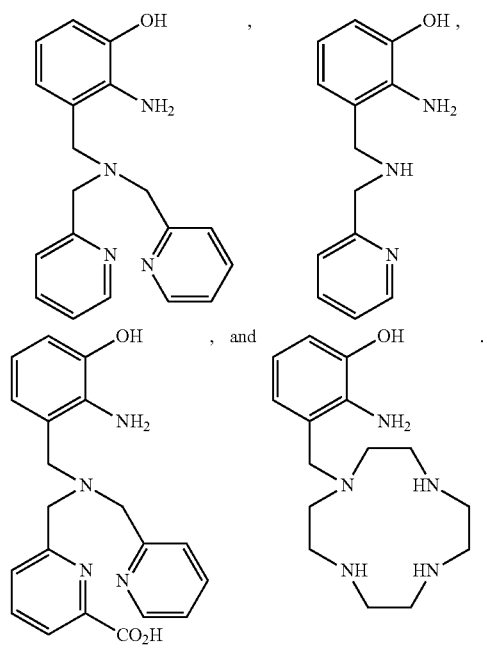

3. The method of claim 1, where the protected compound is prepared by reacting a dihydroxybenzaldehyde with a hydroxymethyl group defined by:

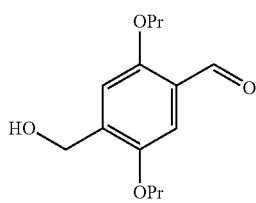

where each Pr is individually a protecting group, with a an aminobenzene derivative defined by the formula:

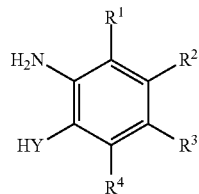

where Y is an oxygen atom, a sulfur atom, a nitrogen atom with a pendant hydrogen atom, and $R^1$, $R^2$, $R^3$, and $R^4$ are each individually selected from the group consisting of a hydrogen atom, an electron withdrawing group, and an electron donating group.

4. The method of claim 1, where the 2-aminophenol derivative is prepared by
   (i) reacting a nitrobenzene derivative defined by the formula

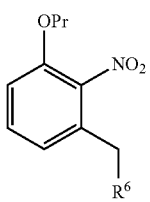

where Pr is a protecting group, and $R^6$ is a halogen atom or a tosyl group, with a amine compound that includes a chelating group;
   (ii) deprotecting the protected oxygen atom; and
   (iii) converting the nitro group to an amine.

5. The method of claim 1, where the 2-aminophenol is prepared by
   (i) reacting a nitrobenzene derivative defined by the formula

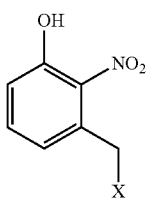

where X is a halogen, with a amine compound that includes a chelating group; and
   (ii) converting the nitro group to an amine.

6. A process for preparing a Zinhbo derivative comprising:
   (i) reacting a protected compound defined by the formula:

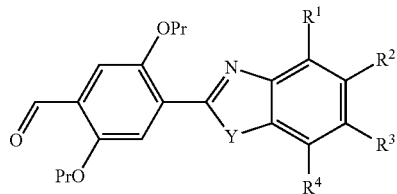

where Y is an oxygen atom, a sulfur atom, a nitrogen atom with a pendant hydrogen atom, or a nitrogen atom with a pendant alkyl group; each Pr is individually a protecting group and $R^1$, $R^2$, $R^3$, and $R^4$ are each individually selected from the group consisting of a hydrogen atom, an electron withdrawing group, and an electron donating group, with a 2-aminophenol derivative defined by the formula

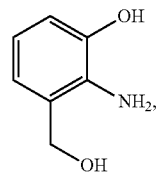

via a process that includes an oxidation reaction, to prepare a molecule defined by the formula I:

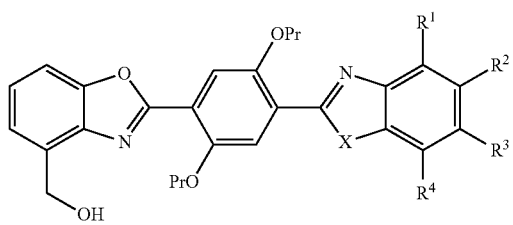

where each Pr is individually a protecting group, Y is an oxygen atom, a sulfur atom, a nitrogen atom with a pendant hydrogen atom, or a nitrogen atom with a pendant alkyl group, and $R^1$, $R^2$, $R^3$, and $R^4$ are each individually selected from the group consisting of a hydrogen atom, an electron withdrawing group, and an electron donating group;
   (ii) converting the OH group of formula I to a halogen atom or tosyl group;
   (iii) reacting the halogen atom or tosyl group with a an amine compound that includes a chelating group;
   (iv) deprotecting the protecting groups to form a Zinhdo derivative defined by the following formula:

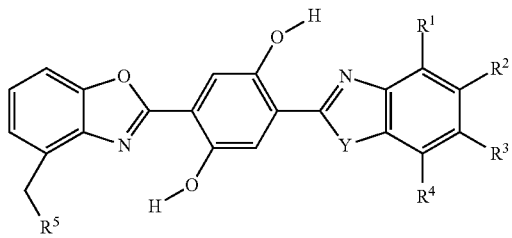

where $R^1$, $R^2$, $R^3$, and $R^4$ are each individually selected from the group consisting of a hydrogen atom, an electron withdrawing group, and an electron donating group; Y is an oxygen atom, a sulfur atom, a nitrogen atom with a pendant hydrogen atom, or a nitrogen atom with a pendant alkyl group; and $R^5$ is a chelating group attached through a nitrogen atom.

7. The method of claim 6, where the amine compounds that includes a chelating group is selected from di-2-picolylamine, 1,4,7,10-tetrazacyclododecane, and pyridin-2-yl-methyl)amine.

8. The method of claim 6, where formula 1 is produced by reacting the protected compound with the 2-aminophenol derivative in the presence of oxygen.

9. The method of claim 8, were the protected compound and the 2-aminophenol derivative in the presence of oxygen in a solvent at 110 to 120° C. for about 2 to 4 hr.

10. A process for preparing a Zinhbo derivative comprising:
(i) reacting a protected compound defined by the formula:

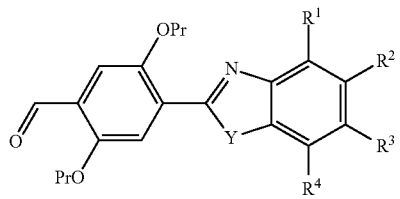

where Y is an oxygen atom, a sulfur atom, a nitrogen atom with a pendant hydrogen atom, or a nitrogen atom with a pendant alkyl group; each Pr is individually a protecting group and $R^1$, $R^2$, $R^3$, and $R^4$ are each individually selected from the group consisting of a hydrogen atom, an electron withdrawing group, and an electron donating group, with a 2-aminophenol derivative defined by the formula

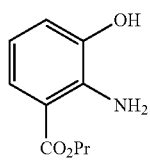

where Pr is a protecting group, via a process that includes an oxidation reaction, to prepare a molecule defined by formula I:

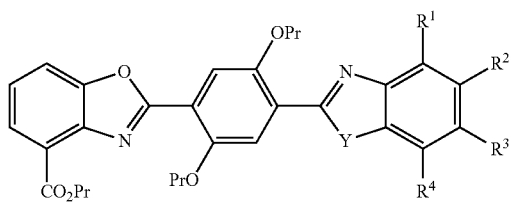

where each Pr is individually a protecting group Y is an oxygen atom, a sulfur atom, a nitrogen atom with a pendent hydrogen atom, or a nitrogen atom with a pendant alkyl group, and $R^1$, $R^2$, $R^3$, and $R^4$ are each individually selected from the group consisting of a hydrogen atom, an electron withdrawing group, and an electron donating group;

(ii) converging the $CO_2Pr$ group of formula I to a $CH_2OH$ group;
(iii) converting the OH group of the $CH_2OH$ group of step (ii) to a halogen atom or tosyl group;
(iv) reacting the halogen atom or tosyl group with an amine compound that includes a chelating group;
(v) deprotecting the protecting groups to form a Zinhbo derivative defined by the following formula:

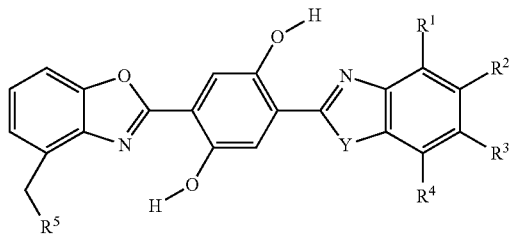

where $R^1$, $R^2$, $R^3$, and $R^4$ are each individually selected from the group consisting of a hydrogen atom, an electron withdrawing group, and an electron donating group; Y is an oxygen atom, a sulfur atom, a nitrogen atom with a pendant hydrogen atom, or a nitrogen atom with a pendant alkyl group; and $R^5$ is a chelating group attached through a nitrogen atom.

11. The method of claim 10, wherein the amine compound-that includes a chelating group is selected from di-2-picolylamine, 1,4,7,10-tetrazacylododecane, and pyridine-2-ylmethyl)amine.

12. The method of claim 10, where formula 1 is produced by reacting the protected compound with the 2-aminophenol derivative in the presence of oxygen.

13. The method of claim 12, were the protected compound and the 2-aminophenol derivative in the presence of oxygen in a solvent at 110 to 120° C. for about 2 to 4 hr.

* * * * *